US011717587B2

(12) United States Patent
Trevor et al.

(10) Patent No.: US 11,717,587 B2
(45) Date of Patent: Aug. 8, 2023

(54) ULTRAVIOLET CLEANING TRAJECTORY MODELING

(71) Applicant: Robust AI, Inc., Palo Alto, CA (US)

(72) Inventors: Alexander Jay Bruen Trevor, San Francisco, CA (US); Dylan Bourgeois, San Francisco, CA (US); Marina Kollmitz, Freiburg (DE); Crystal Chao, San Francisco, CA (US)

(73) Assignee: Robust AI, Inc., Palo Alto, CA (US)

( * ) Notice: Subject to any disclaimer, the term of this patent is extended or adjusted under 35 U.S.C. 154(b) by 267 days.

(21) Appl. No.: 17/207,195

(22) Filed: Mar. 19, 2021

(65) Prior Publication Data
US 2021/0347048 A1  Nov. 11, 2021

Related U.S. Application Data

(60) Provisional application No. 63/022,349, filed on May 8, 2020, provisional application No. 63/022,348, filed on May 8, 2020.

(51) Int. Cl.
*B25J 9/16* (2006.01)
*B25J 11/00* (2006.01)
(Continued)

(52) U.S. Cl.
CPC ........... *A61L 2/24* (2013.01); *A47L 11/405* (2013.01); *A47L 11/4011* (2013.01); *A61L 2/10* (2013.01); *B25J 9/1664* (2013.01); *B25J 9/1674* (2013.01); *B25J 11/0085* (2013.01); *B25J 15/0014* (2013.01); *B25J 18/00* (2013.01);
(Continued)

(58) Field of Classification Search
CPC ...... B25J 11/0085; B25J 9/162; B25J 9/1664; B25J 9/1666; B25J 9/1679; B25J 9/1684; B25J 9/1694; B25J 9/1697; B25J 9/1674; B25J 9/1676; A61L 2/08–12; A61L 2202/11; A61L 2202/14; A61L 2202/16;
(Continued)

(56) References Cited

U.S. PATENT DOCUMENTS 4,028,135 A   6/1977  Vig et al.
6,865,446 B2  3/2005  Yokono et al.
(Continued)

FOREIGN PATENT DOCUMENTS

WO   2018233853 A1   12/2018
WO   2018233858 A1   12/2018

OTHER PUBLICATIONS

Int'l Application Serial No. PCT/US21/24416, Int'l Search Report and Written Opinion dated Jun. 10, 2021.
(Continued)

Primary Examiner — Spencer D Patton
(74) Attorney, Agent, or Firm — Polygon IP, LLP

(57) ABSTRACT

A model of a physical environment may be determined based at least in part on sensor data collected by one or more sensors at a robot. The model may include a plurality of constraints and a plurality of data values. A trajectory through the physical environment may be determined for an ultraviolet end effector coupled with the robot to clean one or more surfaces in the physical environment. The ultraviolet end effector may include one or more ultraviolet light sources. The ultraviolet end effector may be moved along the trajectory.

14 Claims, 16 Drawing Sheets

(51) Int. Cl.

| | |
|---|---|
| A61L 2/24 | (2006.01) |
| A61L 2/10 | (2006.01) |
| A47L 11/40 | (2006.01) |
| B25J 15/00 | (2006.01) |
| G02B 3/08 | (2006.01) |
| G02B 5/20 | (2006.01) |
| G02B 5/26 | (2006.01) |
| G02B 26/08 | (2006.01) |
| G05D 1/00 | (2006.01) |
| G05D 1/02 | (2020.01) |
| B25J 18/00 | (2006.01) |
| G01C 21/20 | (2006.01) |

(52) U.S. Cl.
CPC ............ *G01C 21/206* (2013.01); *G02B 3/08* (2013.01); *G02B 5/208* (2013.01); *G02B 5/26* (2013.01); *G02B 26/0875* (2013.01); *G05D 1/0094* (2013.01); *G05D 1/0214* (2013.01); *G05D 1/0246* (2013.01); *A47L 2201/04* (2013.01); *A61L 2202/11* (2013.01); *A61L 2202/14* (2013.01); *A61L 2202/16* (2013.01); *A61L 2202/17* (2013.01); *A61L 2202/25* (2013.01); *G05B 2219/50391* (2013.01); *G05D 2201/0203* (2013.01)

(58) Field of Classification Search
CPC ........ A61L 2202/25; G05D 2201/0203; A47L 11/4011; A47L 11/405
See application file for complete search history.

(56) References Cited

U.S. PATENT DOCUMENTS

| | | | |
|---|---|---|---|
| 6,925,679 | B2 | 8/2005 | Wallach et al. |
| 8,428,781 | B2 | 4/2013 | Chang et al. |
| 8,909,370 | B2 | 12/2014 | Stiehl et al. |
| 9,757,486 | B2 | 9/2017 | Dobrinsky et al. |
| 10,279,476 | B2 | 5/2019 | Jaekel et al. |
| 10,793,291 | B2 | 10/2020 | Brown et al. |
| 11,548,159 | B1 * | 1/2023 | Ebrahimi Afrouzi ..... G06T 5/50 |
| 2016/0271803 | A1 * | 9/2016 | Stewart ................ B25J 11/0085 |
| 2016/0354931 | A1 | 12/2016 | Jones et al. |
| 2017/0097232 | A1 * | 4/2017 | Anderson-Sprecher .................... G01C 21/383 |
| 2017/0246331 | A1 * | 8/2017 | Lloyd .................... A61Q 17/04 |
| 2018/0104368 | A1 | 4/2018 | Dobrinsky et al. |
| 2018/0116479 | A1 | 5/2018 | Gilbert, Jr. et al. |
| 2018/0161986 | A1 * | 6/2018 | Kee ......... G06F 18/29 |
| 2019/0219409 | A1 | 7/2019 | Tan et al. |
| 2019/0224853 | A1 | 7/2019 | Gewecke et al. |
| 2020/0086487 | A1 | 3/2020 | Johnson et al. |
| 2020/0094418 | A1 | 3/2020 | Mika et al. |
| 2021/0053207 | A1 | 2/2021 | Romanov et al. |
| 2022/0088237 | A1 * | 3/2022 | Hauser ................. G06T 15/506 |

OTHER PUBLICATIONS

Huang, Feixiang; Robotic Delivery System for Material Handling [Master's Thesis, University of Akron], Dec. 2014.

Mobile Autonomous Robotic Cart 3 Series Overview, 3 Series Data Sheet V220301A, retrieved on Jul. 22, 2022, https://www.multechnologies.com/hubfs/manuals/MARC_3_Series_data_sheet_2203a.pdf.

Scholz, Jonathan et al.; Cart Pushing with a Mobile Manipulation System: Towards Navigation with Moveable Objects, retrieved on Jul. 7, 2022, https://www.cs.cmu.edu/~maxim/files/cartplanner_icra11.pdf.

Wang, Ziyu; Autonomous Robotic Cart for Food Delivery on Airplane, [Master's Thesis, NYU Tandon School of Engineering], Fall 2017, retrieved on Jul. 22, 2022 http://engineering.nyu.edu/mechatronics/projects/MSprojects/2017-2018/4/report.pdf.

* cited by examiner

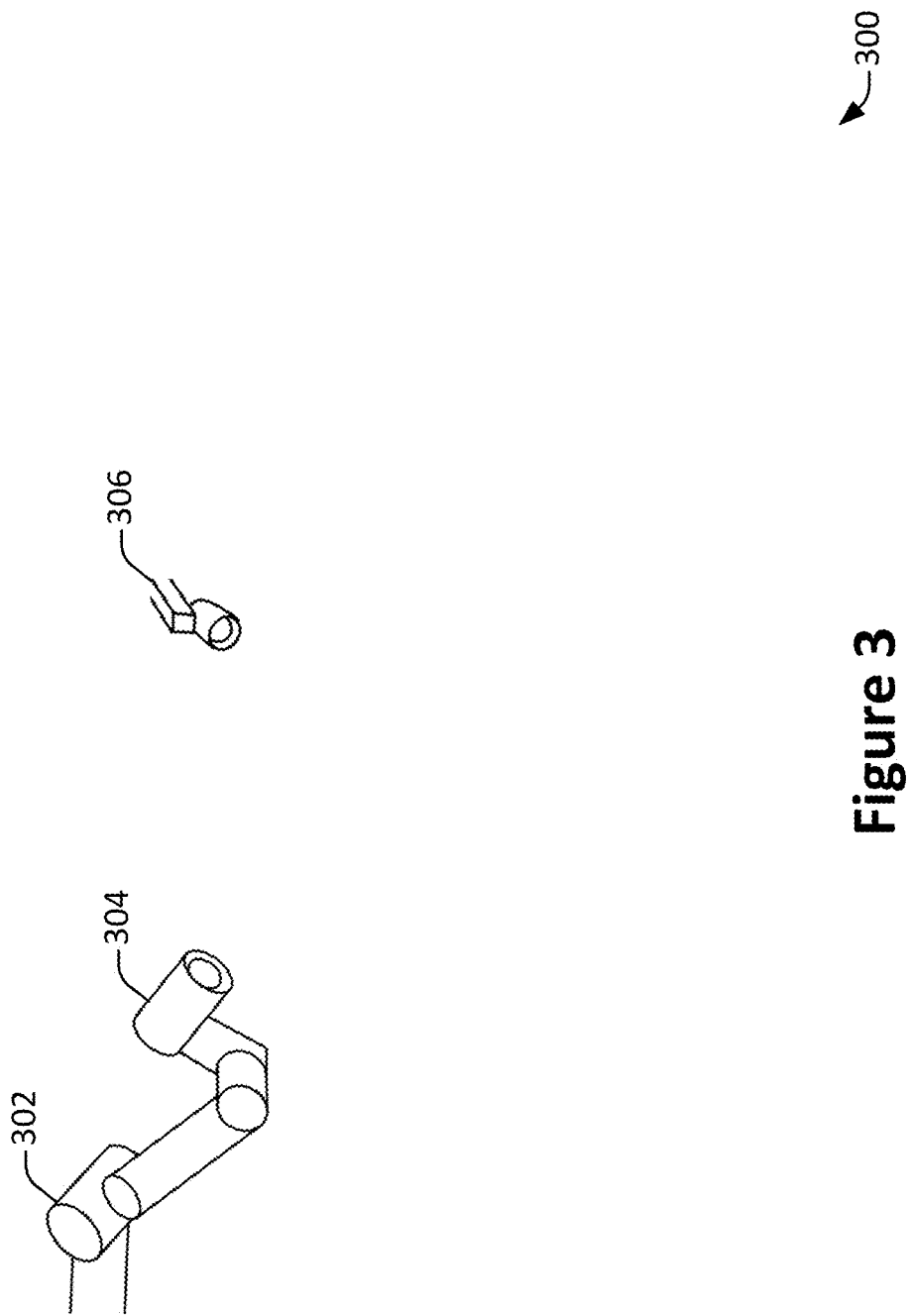

ULTRAVIOLET CLEANING TRAJECTORY MODELING

CROSS-REFERENCE TO RELATED APPLICATION

The present application claims priority under 35 U.S.C. 120 to U.S. Provisional Application No. 63/022,348 by Brooks et al., titled "A CLEANING ROBOT", filed May 8, 2020, and to U.S. Provisional Application No. 63/022,349 by Brooks et al., titled "ROBOTIC SOCIAL INTERACTION", filed May 8, 2020, both of which are hereby incorporated by reference in their entirety and for all purposes.

COPYRIGHT NOTICE

A portion of the disclosure of this patent document contains material which is subject to copyright protection. The copyright owner has no objection to the facsimile reproduction by anyone of the patent document or the patent disclosure as it appears in the United States Patent and Trademark Office patent file or records but otherwise reserves all copyright rights whatsoever.

TECHNICAL FIELD

The present disclosure relates generally to robotics, and more specifically to robotic cleaning solutions.

DESCRIPTION OF RELATED ART

Conventional approaches to cleaning often involve manual activity by humans, but such approaches have numerous drawbacks. For example, humans can clean surfaces using chemical means. However, manual cleaning with chemicals can expose humans to potentially dangerous chemicals and pathogens. Further, manual cleaning with chemicals often results in incomplete cleaning that falls far short of standards for sterilization or even disinfection. As another example, humans can clean surfaces by activating a handheld UV light source. However, such an approach risks exposing humans to excessive UV energy, risks incomplete cleaning, and requires significant manual activity.

Other conventional approaches to cleaning involve automated, powerful UV light sources. However, such an approach often involves moving a powerful light source into an area and then evacuating the area while the cleaning is completed. Such approaches are typically restricted to optically-sealed rooms or shelters from which all people and animals must leave while cleaning occurs. The risk to humans is significant since a safe dosage would be exceeded at 1 meter distance in a matter of seconds. In addition, such approaches require massive energy consumption. Such powerful UV light sources also can degrade plastics, equipment, and other materials present in the room. Some powerful UV lamps emit ozone, a greenhouse gas. Alternatively, or additionally, some powerful UV lamps contain mercury (Hg), which both creates sanitary risks and imposes an environmental cost.

OVERVIEW

According to various embodiments, techniques and mechanisms described herein provide for systems, devices, methods, and machine readable media for robotic cleaning solutions. A model of a physical environment may be determined based at least in part on sensor data collected by one or more sensors at a robot. The model may include a plurality of constraints, the model further including a plurality of data values. A trajectory through the physical environment for an ultraviolet end effector coupled with the robot to clean one or more surfaces in the physical environment may be determined based on the model. The ultraviolet end effector may include one or more ultraviolet light sources. The ultraviolet end effector may be caused to move along the trajectory.

In some implementations, the model may include a plurality of original uncertainty values that each express a statistical dispersion around a respective one of a subset of the data values. Determining the trajectory may involve determining a plurality of updated data values that each correspond with a respective one of the subset of the data values. The uncertainty values may account for a location uncertainty regarding one or more initial location values associated with the ultraviolet end effector, and determining the trajectory may involve reducing the location uncertainty. The determined trajectory may be consistent with the uncertainty values. The model may be encoded as a factor graph.

According to various embodiments, the plurality of constraints may include a field of view constraint indicating a field of view associated with the ultraviolet end effector. The plurality of constraints may include a visibility constraint associated with the physical environment. The visibility constraint may indicate a physical occlusion within the physical environment. The plurality of constraints may include a safety constraint that indicates an actual or predicted location associated with a human being within the physical environment.

According to various embodiments, each of the constraints may be associated with a respective relative importance value within the model, the trajectory may be determined at least in part based on the relative importance values. The plurality of constraints may include a kinematic constraint indicating a physical limitation associated with the movement of the robot through the physical environment. The plurality of constraints may include a designated level of ultraviolet light to be received by the one or more surfaces. The designated level of ultraviolet light may be determined based on an identity of one or more pathogens to be cleaned from the one or more surfaces. The plurality of constraints may include an energy constraint indicating a level of energy capable of being expended by the robot.

According to various embodiments, the model may include a cost function identifying a virtual cost associated with a time associated with the determined trajectory. Determining the trajectory may involve reducing the time based on the cost function. The model may include a cost function identifying a virtual cost associated with one or more types of movement by the robot. Determining the trajectory may involve reducing movement based on the cost function.

BRIEF DESCRIPTION OF THE DRAWINGS

The included drawings are for illustrative purposes and serve only to provide examples of possible structures and operations for the disclosed inventive systems, apparatus, methods and computer program products for robotic cleaning solutions. These drawings in no way limit any changes in form and detail that may be made by one skilled in the art without departing from the spirit and scope of the disclosed implementations.

FIG. 3 illustrates a UV end effector calibration system, configured in accordance with one or more embodiments.

DETAILED DESCRIPTION

Figure 1:
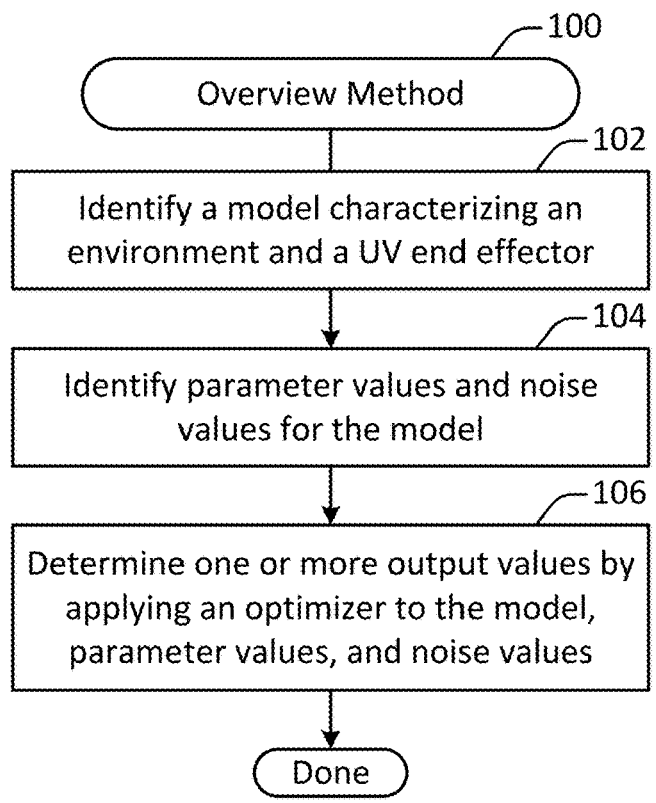
FIG. 1 illustrates an overview method, performed in accordance with one or more embodiments.

Techniques and mechanisms described herein are directed to models employed in conjunction with a robotic cleaning solution. A robot may navigate an area for the purpose of cleaning some or all of the area. The area may be otherwise occupied by people who are present for purposes associated with the location. Accordingly, the robot may engage in social accommodation, in which it attempts to accomplish its cleaning task while taking into account the presence, goals, and trajectories of the people.

According to various embodiments, the robot may be equipped with one or more cleaning tools, such as one or more ultraviolet (UV) power sources. The term "UV light" generally refers to electromagnetic radiation in the 10 nm-400 nm wavelength range. Cleaning applications of UV radiation, sometimes referred to as Ultra-Violet Germicidal Irradiation (UVGI), can apply illumination in the UVC range of wavelengths, between approximately 100 nm-280 nm, corresponding to the range of maximum response by most targeted pathogens.

In some implementations, one or more UV light sources may be configured with one or more additional components to form a UV end effector. These additional components may serve to direct, focus, reflect, deform, refract, or otherwise manipulate one or more UV light source and/or the UV light emitted by one or more UV light sources.

According to various embodiments, depending on the configuration, a cleaning tool such as a UV end effector may be oriented in one, two, three, four, five, six, or any number of suitable dimensions, independent of the movement of the robot itself. For example, a robot may position a UV end effector close to a cleaning target and then activate the UV light source. The robot may then move the UV end effector through a trajectory, either by moving the end effector, moving the robot, or some combination thereon.

According to various embodiments, techniques and mechanisms described herein provide for models that may be employed for various functions related to robotic cleaning. For example, a model may be employed to determine a trajectory for a UV end effector and/or the robot itself through a virtual environment. As another example, a model may be employed to configure a UV end effector and/or one or more UV light sources. As yet another example, a model may be employed to estimate or predict a level of UV exposure.

According to various embodiments, the robot may be equipped to accommodate the presence of people within the area of cleaning. For example, the robot may monitor people nearby and estimate levels of UV radiation the people may be receiving. If the robot determines that radiation may bring the total dose to any human above a safety threshold, then the robot may avoid activating the UV power source or may deactivate the UV power source if it has already been activated. As another example, the robot may provide social cues to people as to the robot's actions. For instance, the robot may indicate what it is doing and/or how long the cleaning action will continue. As yet another example, the robot may interrupt a cleaning process and/or move to a different location when it determines that it should defer to the activity of humans, animals, or other robots.

In some implementations, the robot may be guided in its cleaning activity based on communication with a remote computing device such as a control computer having access to a database system. Alternatively, or additionally, the robot may report its actions to such a system.

In some implementations, the robot may coordinate with other robots. The other robots may be configured to perform complementary cleaning activities or may be focused on other tasks. Each robot may be directed by a central command and control apparatus. Alternatively, or additionally, the robots may communicate with each other directly.

In some implementations, the robot may communicate with nearby people. For example, the robot may receive cleaning instructions from a nearby person. As another example, the robot may receive instructions about social accommodation from a nearby person. The robot may be configured to verify the authority of the person to issue such instructions. For instance, the robot may be configured to ascertain the person's identity and/or role through any of various authentication mechanisms.

In some embodiments, the term "cleaning" may encompass any or all of a variety of concepts. At the lowest level, "sanitation" refers to reducing the density amount of pathogenic microbes on a surface. The term "disinfection" refers to a strong sanitization in which specific pathogens are almost totally removed. "Decontamination" refers to the removal of specific dangerous pathogens. At the highest level, "sterilization" refers to the removal of all pathogens from a surface. The term "power" refers to energy over time and may be measured in Watts (i.e., Joules/second). The term "intensity" refers to the amount of power distributed on a surface and may be measured in Watts per area of surface. The term "dose" refers to intensity received over time and may be measured in Joules per area of surface, or equivalently Watts multiplied by time and divided by surface area.

In contrast to conventional approaches, techniques and mechanisms described herein provide for the safe, effective, comprehensive, and automated cleaning. For example, techniques and mechanisms described herein may facilitate the automated cleaning of a hospital, laboratory, restaurant, retail establishment, industrial facility, schools, or other environments.

In some implementations, one or more cleaning robots may navigate a physical environment to clean surfaces and objects within the environment. For example, each cleaning robot may be equipped with one or more relatively low power, directional UV light sources that the robot brings into close proximity with a surface to be cleaned. Because the UV light source is relatively lower powered and/or directional, human exposure can be limited or prevented. For instance, the robot can monitor the environment to avoid both inconveniencing humans and exposing humans to excessive UV energy. The robot can then automatically navigate to a charging or docking station when its tasks have been completed.

In particular embodiments, techniques and mechanisms described herein may facilitate the cleaning of an environment such as a hospital. The complexity, number of pathogens, and high occupancy of hospital environments makes the cleaning of such environments both extremely important and yet difficult via conventional means. However, using techniques and mechanisms described herein, one or more robots may continuously or periodically traverse a hospital environment to clean objects and surfaces. In particular, a robot using a targeted, low-powered UV light source may unobtrusively and safely navigate the environment to opportunistically clean surfaces and objects when such cleaning can be performed without inconveniencing humans or exposing humans to excessive UV radiation.

In particular embodiments, a cleaning robot can also perform tasks in a socially aware way, for instance by recognizing individuals based on their roles as doctors, nurses, patients, administrators, maintenance workers, and/or members of the public, and then treating individuals differently based on those roles. For example, the cleaning robot may place a very high priority on avoiding doctors and nurses, who may be in a hurry to provide medical services. As another example, the cleaning robot may be configured to respond to instructions from maintenance workers and administrators. However, the cleaning robot may be less accommodating of other individuals, such as members of the general public.

FIG. 1 illustrates an overview method 100, performed in accordance with one or more embodiments. According to various embodiments, the method 100 may be performed to determine any or all of a variety of different types of information. For example, the method 100 may be used to determine a planned trajectory for a UV end effector. As another example, the method 100 may be used to determine an estimated UV exposure level for a person, surface, or other object in a physical or simulated environment. As yet another example, the method 100 may be used to determine a configuration of light sources to employ within a UV end effector.

In some implementations, the method 100 may be initiated based upon user input. For instance, a user may request to determine a configuration of light sources to employ within a UV end effector.

In some implementations, the method 100 may be initiated automatically. For instance, a robot may autonomously initiate the method 100 in order to determine a trajectory for cleaning one or more surfaces within a physical environment or to determine an estimated UV exposure for a person, surface, or other object in an environment.

A model characterizing an physical environment and a UV end effector is identified at 102. Parameter values and noise values for the model are identified at 104. An example of the type of model that may be employed is discussed in further detail with respect to FIG. 2.

In some implementations, the model and/or associated values may be determined at least in part based on sensor data collected at a robot. For instance, the robot may employ one or more cameras, depth sensors, or other sensors to construct a model of a physical environment.

In some embodiments, the model and/or associated values may be determined at least in part based on simulation data. For instance, a model may include one or more parameter values indicating the locations of virtual objects within a virtual space.

In some embodiments, the model and/or associated values may be determined based at least in part on user input. For instance, a user may specify one or more parameter values or associated noise values.

In some embodiments, the model and/or associated values may be determined based at least in part on predetermined calibration information. For example, a UV end effector may be calibrated as discussed with respect to FIGS. 3-5. Such information may then be stored for later use, for instance in association with the method 100. As another example, a robot may associated with kinematic information that is provided as an input to the model.

One or more output values are determined at 106 by applying an optimizer to the model, the parameter values, and the noise values. In some implementations, the model may be represented at least in part as a factor graph. Alternatively, or additionally, a neural network may be employed to represent some or all of the representations in the model.

According to various embodiments, one or more of a variety of loss functions may be employed when applying the optimizer. Such loss functions may include, but are not limited to: least squares, quantile loss, quadratic loss, and smooth mean absolute error. In particular embodiments, the loss function may be strategically determined based on one or more of a variety of considerations. For instance, when a human is present in an environment, a more conservative loss function may be employed to reduce the likelihood of outliers when calculating ultraviolet light exposure to the human.

According to various embodiments, one or more of a variety of optimization approaches may be employed. For instance, in the non-linear least squares case, these optimization approaches may included, but are not limited to: Levenberg-Marquardt, Gauss-Newton, and Kowalski decomposition.

Figures 2A, 2B:
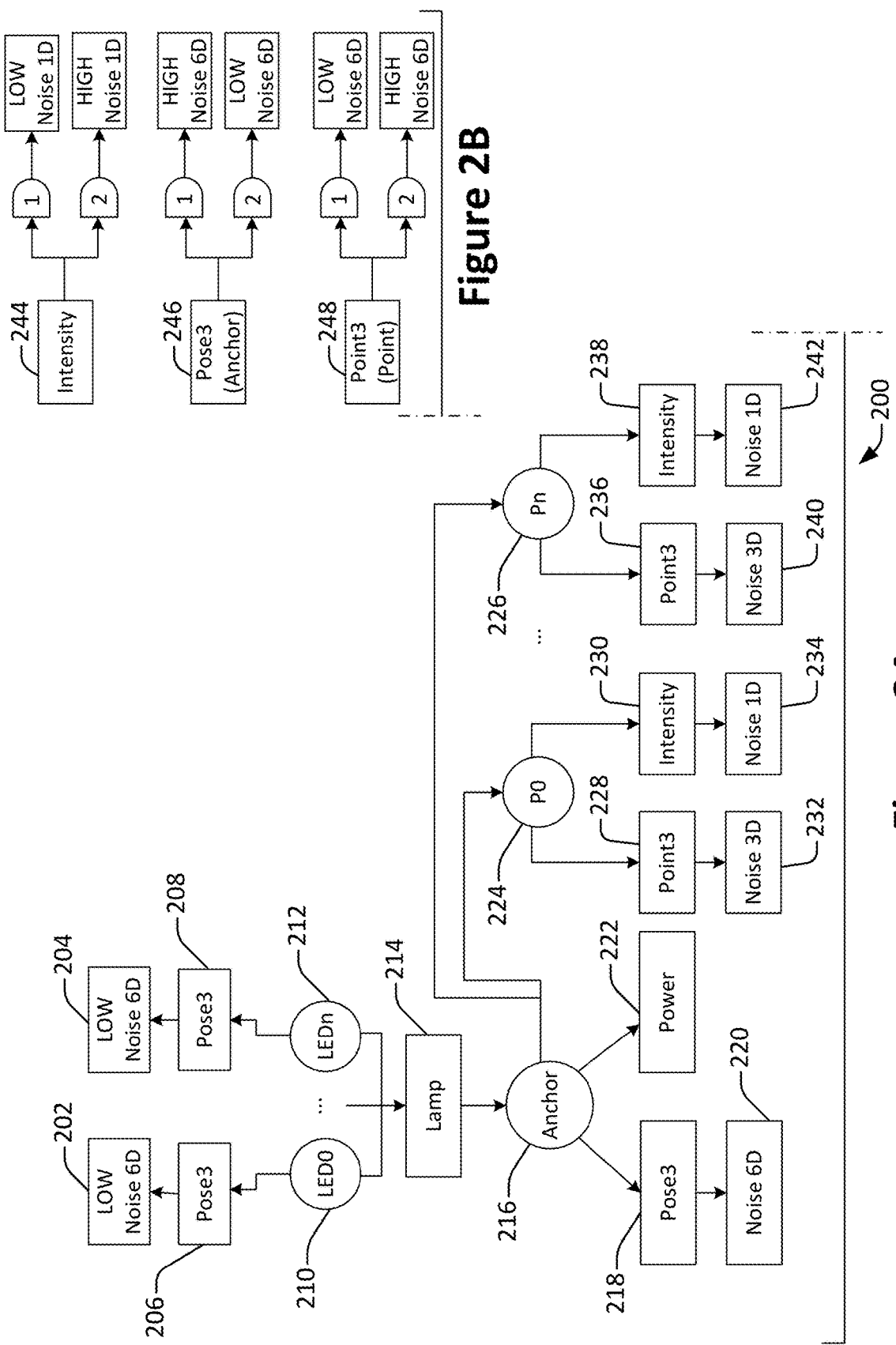
FIGS. 2A and 2B illustrate diagrams of a model, generated in accordance with one or more embodiments.

FIG. 2 illustrates a diagram of a model 200, generated in accordance with one or more embodiments. The model 200 is an example of a configuration in which an LED UV end effector having n light sources may be positioned in space and activated to expose a surface to UV light.

The model 200 includes pose values 206 through 208 for LED light sources 210 through 212. Each of these pose values is associated with a respective noise level 202 through 204. According to various embodiments, a pose value and its associated noise value may be specified in up to three dimensions for position and up to three dimensions for orientation. The values associated with the LEDs may be aggregated at 214.

According to various embodiments, a noise value may be specified in any of a variety of ways. For example, noise may be represented as a standard deviation, statistical distribution, variance, or other such approach. Noise values may be specified for pose dimensions individually or via a joint value or distribution.

According to various embodiments, an anchor 216 may aggregate various values associated with the UV end effector. For example, the poses of the individual light sources may be aggregated into a single pose value 218 and associated noise value 220 for the UV end effector as a whole. As another example, in the model 200, a common power value 222 is used for all of the LEDs rather than controlling the LED power individually. However, in a different configuration, LED power values may be individually controlled.

According to various embodiments, each of the points P0 224 through Pm 226 may correspond to a point in space, such as a point on a surface, to be exposed or not exposed to UV light. For example, one subset of the points may correspond to a surface to be cleaned, while another subset of the points may correspond to a surface of a human that is not to be exposed to UV light (e.g., above a designated threshold).

According to various embodiments, each of the points P0 224 through Pm 226 is associated with a respective position value, such as the position values 228 and 236. Each of these position values are associated with a respective noise value such as the noise values 232 and 240. The noise values represent uncertainty about the location of those points in space.

According to various embodiments, each of the points P0 224 through Pm 226 is associated with a respective intensity value, such as the intensity values 230 and 238. Each intensity value is associated with a respective noise value such as the noise values 234 and 242.

According to various embodiments, a model may have more, fewer, or different elements than those shown in FIG. 2. For instance, a model may include parameters for the position and/or orientation of a robot, and separate parameters for the position and/or orientation of a robotic arm that is coupled with the robot and the UV end effector. Additionally, different parameters may be associated with costs so that, for instance, the robot in practice prefers to move its robotic arm rather than the entire robot to reposition the UV end effector.

In particular embodiments, the optimizer may be applied to determine more precise updated values for initial values associated with high noise values. For example, as shown at 246, to determine a trajectory along which a UV end effector may travel to clean a designated surface, a model may be specified with relatively precise (i.e., low noise) values for parameters such as surface locations within a physical environment, UV end effector intensity patterns, robot kinematic constraints, UV exposure levels for the designated surface, and other such characteristics. At the same time, the model may be specified with relatively imprecise (i.e., high noise) values for UV end effector pose (e.g., position and/or orientation) values over time. The optimizer may then identify UV end effector position and/or orientation values over time that fit the other parameters of the model. Such an approach is discussed in further detail with respect to the method 600 shown in FIG. 6.

As another example, to determine a pattern (e.g., position, number, and/or orientation) for light sources on a UV end effector, a model may be specified with relatively precise values for parameters such as UV exposure levels for a designated surface, UV end effector position and/or orientation values over time, and other such characteristics. At the same time, the model may be specified with relatively imprecise parameters for variables such as the position, number, and/or orientation of UV light sources on a UV end effector. The optimizer may then identify values for position, number, and/or orientation of UV light sources that fit the other parameters of the model. Such an approach is discussed in further detail with respect to the method 700 shown in FIG. 7. For instance, at 248, an intensity pattern for a UV end effector is determined.

As yet another example, as shown at 244, to determine an estimated past, current, or future UV exposure level for a human or other object within a physical or virtual environment, a model may be specified with relatively precise values for parameters such as surface locations within a physical environment, UV end effector intensity patterns, UV end effector position and orientation over time, and other such characteristics. At the same time, the model may be specified with relatively imprecise parameters for variables such as UV exposure on various points on the surface of the human or other object. The optimizer may then identify values for the UV exposure on those points that fit the other parameters of the model. Such an approach is discussed in further detail with respect to the method 1000 shown in FIG. 10.

FIG. 3 illustrates a UV end effector calibration system 300, configured in accordance with one or more embodiments. The UV end effector calibration system 300 includes a robotic arm 302 upon which a UV end effector 304 can be positioned. The robotic arm 302 may be moved through space to position the UV end effector 304 at a designated position. The UV end effector 304 may then be activated to project UV light. A light meter 306 may then detect the UV light intensity. The detected UV light intensity may be recorded to build a comprehensive model of the UV light emitted by the UV end effector 304.

According to various embodiments, the robotic arm 302 may be configured to position the UV end effector 304 with up to six degrees of freedom. For example, the robotic arm 302 may be configured to position the UV end effector at any of a variety of locations within a three-dimensional space. As another example, the robotic arm 302 may be configured to orient the UV end effector 304 by altering its roll, pitch, and/or yaw.

In some implementations, the UV end effector calibration system 300 may be configured such as the robotic arm 302 is located at a known position relative to the light meter 306. The robotic arm may then position the UV end effector 304 at a known position in three-dimensional space. Accordingly, the pattern of UV light emitted by the UV end effector may then indicate the intensity of the UV light emitted by the UV end effector 304 at a known distance and orientation in three-dimensional space.

Although the UV end effector calibration system 300 is shown as having the UV end effector 304 arranged in a mobile configuration and the light meter 306 arranged in a fixed configuration, other arrangements are possible. For example, the UV end effector 304 may be fixed, while the light meter 306 may be moved to known points in three-dimensional space around the UV end effector 304. As discussed above, such movement may be performed in up to 6 degrees of freedom, since the light meter 306 may be positioned and oriented in each of up to three dimensions.

In particular embodiments, the UV end effector calibration system 300 may be used to determine a model of UV light emitted by any of a variety of suitable UV light sources. For example, the UV light source may be any UV light source discussed herein, including one or more point, rod, or surface light source. As another example, the UV light source may be a more complex configuration, such as one that involves a Fresnel lens, hinge, or other such component.

Figure 4:
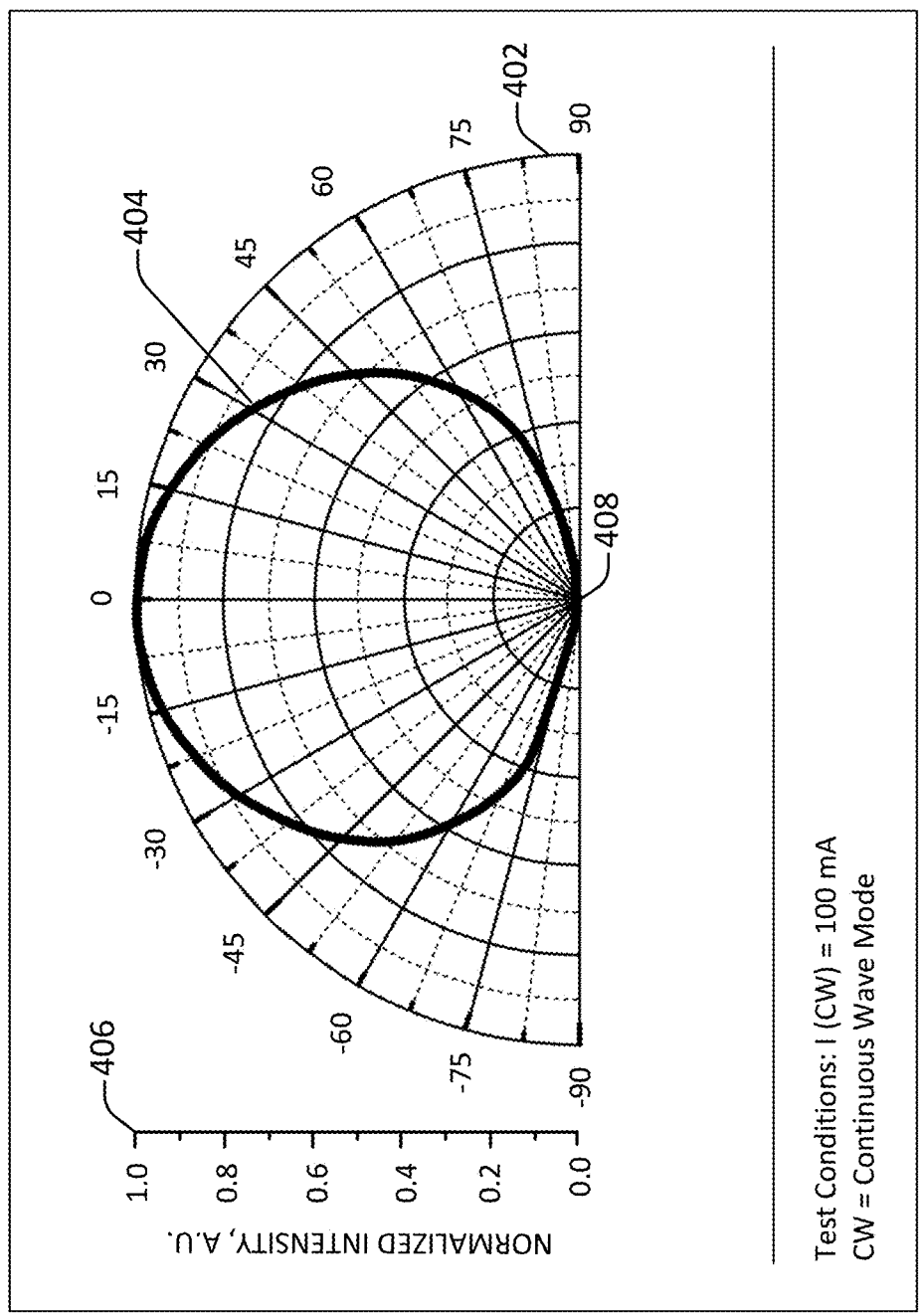
FIG. 4 illustrates an example of a plot of UV intensity determined based on the light source calibration method, performed in accordance with one or more embodiments.

FIG. 4 illustrates an example of a plot 400 of UV intensity determined based on the light source calibration method, performed in accordance with one or more embodiments. The plot 400 illustrates an irradiance pattern in only two dimensions, but in practice more dimensions may be employed. As discussed herein, light sources may be arranged with as many as six degrees of freedom.

The plot 400 illustrates an intensity pattern 404 in polar coordinates. The origin 408 represents the location of the light source. The distance from the origin 408 as indicated by the scale 406 shows the intensity at a designated angle as specified by the angular coordinate axis 402. As shown in FIG. 4, the intensity at a given distance is highest immediately in front of the origin and is lowest as the angular distance increases, trending to zero at 90 degrees.

Figure 5:
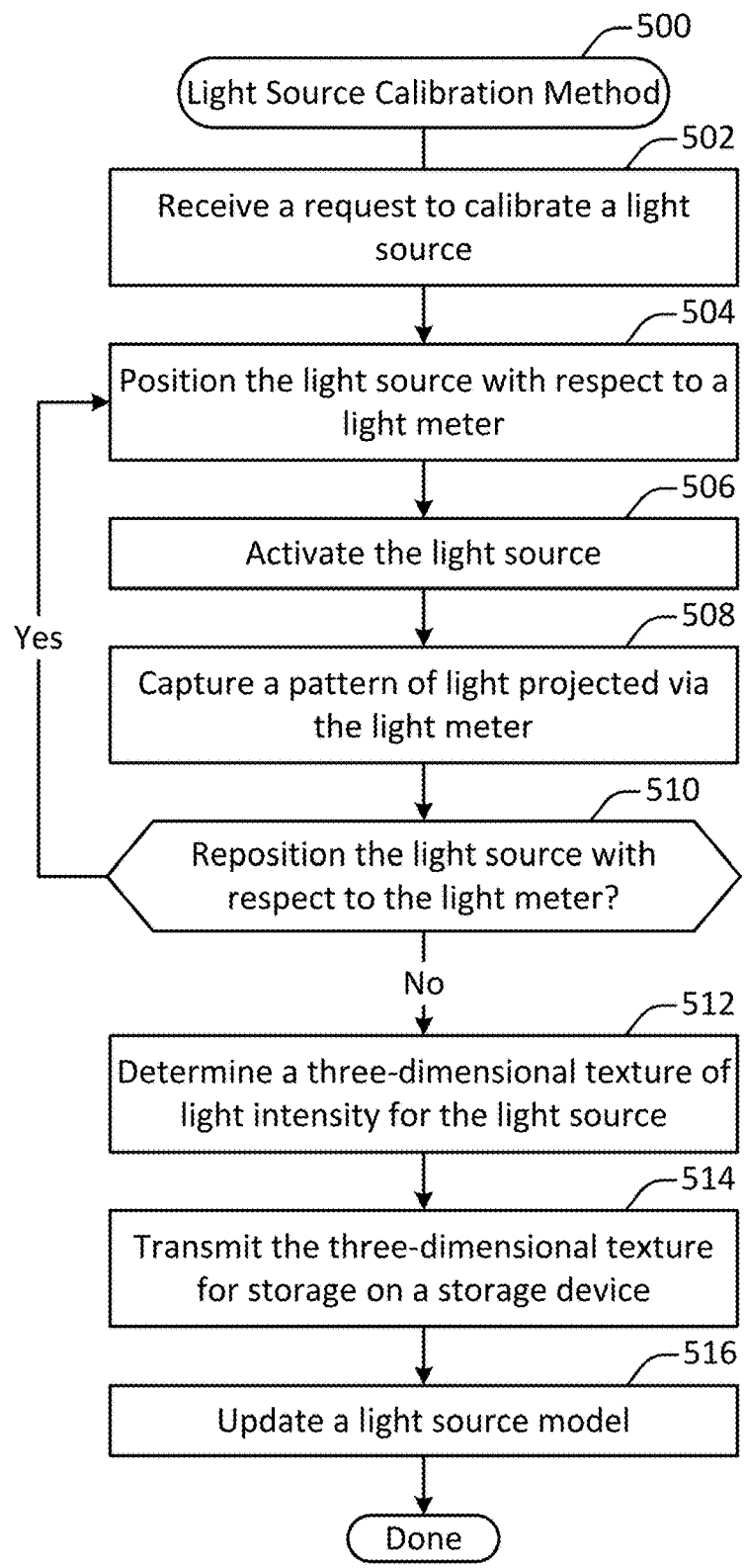
FIG. 5 illustrates a method for calibrating a light source, performed in accordance with one or more embodiments.

FIG. 5 illustrates a method 500 for calibrating a light source, performed in accordance with one or more embodiments. The method 500 may be performed in order to determine a three-dimensional model of intensity for light emitted by a UV light source or any other light source. For instance, the method 500 may be used to determine a three-dimensional model of intensity for light emitted by one or more of the end effectors discussed herein.

In some implementations, the method 500 may be performed in order to employ a light source in a cleaning solution. For instance, the three-dimensional model of intensity may be used to determine a trajectory through space for moving a UV light source in order to clean a surface.

A request to calibrate a light source is received at 502. In some implementations, the request may be received at a light source calibration system such as the system 300 shown in FIG. 3. The light source may be arranged within a UV end effector.

The light source is positioned with respect to a projection screen at 504. According to various embodiments, the light source may be positioned by moving a robotic arm on which the light source is fixed. Alternatively, the projection screen may be positioned relative to a fixed light source. In still another configuration, both the light source and the projection screen may be moved in space.

The light source is activated at 506. When activated, the light source emits UV light onto the screen.

A pattern of light projected through or onto the screen is captured at 506. According to various embodiments, the pattern may be captured by any suitable sensor device. For instance, a sensor device may be configured to detect UV radiation.

A determination is made at 510 as to whether to reposition the light source with respect to the projection screen. According to various embodiments, light sources may be moved through a number of predetermined positions in order to construct a sufficiently comprehensive three-dimensional model of intensity.

In particular embodiments, the determination made at 510 may be made at least in part based on the pattern or patterns captured at 508. For instance, a simple light source may tend to generate relatively simple patterns of projected light. In such a situation, a three-dimensional model may be extrapolated from a relatively small number of positions and patterns. However, a complex end effector may include, for instance, one or more individual light sources, surfaces, lenses, or other such components. Together these components may result in an intensity for the end effector that is complex and non-linear in three or more dimensions, since the intensity at any particular point in space may be determined by a superposition of the emissions of the end effector. Accordingly, as the complexity of the light source increases, so too may the number of positions and patterns needed to accurately determine a three-dimensional model of intensity. Such a situation may be detected based on, for instance, complexity and non-linearity in the detected patterns. For example, the intensity pattern illustrated in FIG. 8A may indicate a relatively simple light source, while the intensity pattern illustrated in FIG. 8C may indicate a more complex light source.

In particular embodiments, positioning the light source may involve placing a UV end effector in a particular configuration. For instance, a UV end effector that includes a hinge, deformable surface, or deformable Fresnel lens may be rotated, adjusted, or deformed to various configurations. In this way, the intensity pattern of a complex light source may be empirically determined by observing the intensity of the light source in various positions, orientations, and configurations.

A three-dimensional texture of light intensity is determined for the light source at 512. In some implementations, the three-dimensional texture of light intensity may serve as a look-up table for the intensity of the source incident on a surface. The three-dimensional texture may be determined by combining information from the patterns captured at 508. For instance, each pattern may represent a cross-section of the light intensity of a plane at the screen's position through the emission of the light source.

The three-dimensional texture is transmitted for storage on a storage device at 514. According to various embodiments, the three-dimensional texture may be stored in any of a variety of formats. For instance, the three-dimensional texture may be stored as a matrix or array of values, as one or more numerical formulas, as one or more gradients, or as some combination thereof.

A light source model is updated at 516. In some implementations, updating the light source model may involve updating one or more values employed in a model such as that discussed with respect to the FIG. 2. For instance, a distribution pattern that is employed in trajectory planning may be updated.

Figure 6:
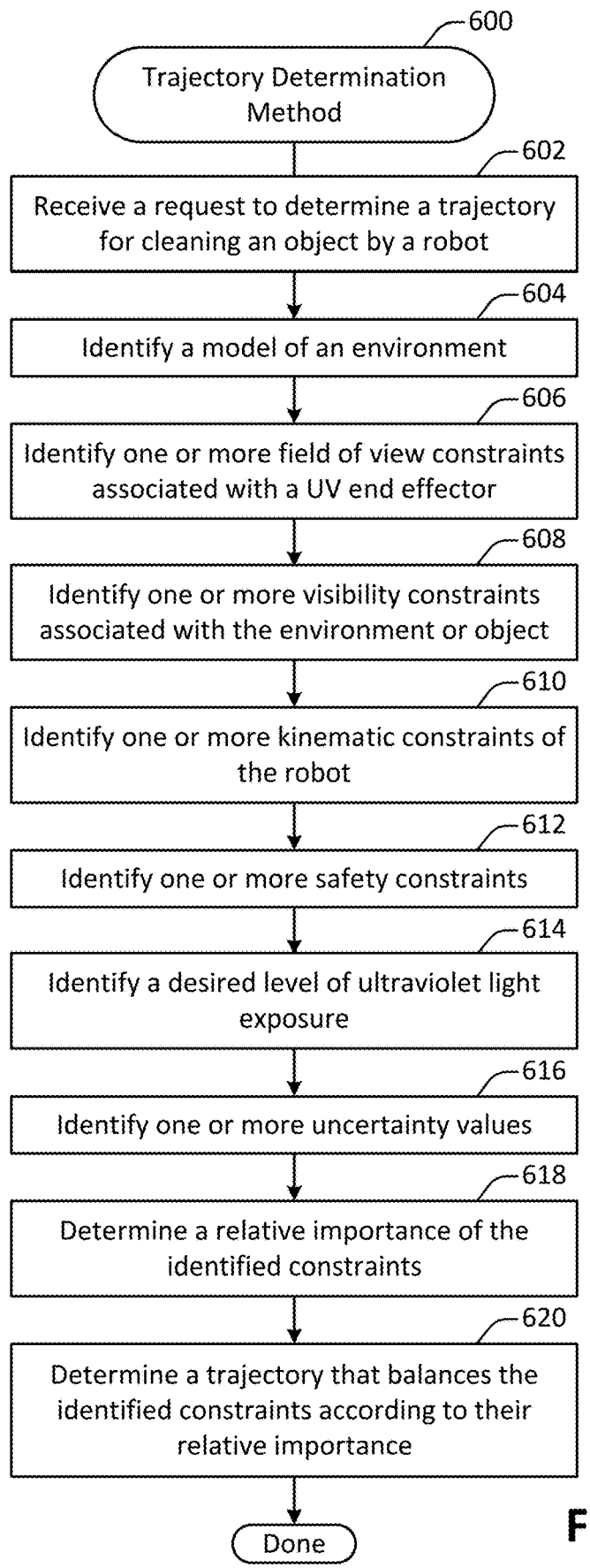
FIG. 6 illustrates a method for determining a trajectory, performed in accordance with one or more embodiments.

FIG. 6 illustrates a method 600 for determining a trajectory, performed in accordance with one or more embodiments. The method 600 may be employed to determine a trajectory through space for a UV end effector to project UV light onto one or more surfaces within a physical or simulated environment.

A request to determine a trajectory for cleaning an object, objects, surface, or surfaces by a robot is determined at 602. According to various embodiments, the request may be determined autonomously as part of the normal operation of the robot. For instance, the robot may be tasked with cleaning surfaces in a particular physical environment after the robot detects that a surface has been touched by a person.

In some implementations, the request may be determined based on user input. For instance, a human may instruct a robot to clean a particular surface within a physical environment.

A model of an environment is determined at 604. As discussed with respect to the operation 102, a model of an environment may be determined based on any or all of a variety of sensor data, computer programming code instructions, and other such input.

One or more field of view constraints associated with a UV end effector are identified at 606. In some implementations, the field of view constraints may indicate, for instance, an intensity pattern associated with light sources arranged on the UV end effector. The determination of such field of view constraints is discussed in additional detail with respect to FIGS. 3-5.

One or more visibility constraints associated with the environment or object are identified at 608. In some implementations, the visibility constraints may be determined at least in part by analyzing the model of the environment identified at 604. One example of a visibility constraint is a physical occlusion that is present within the environment. For instance, the surface of a drawer may be partially obscured by a handle attached to the door. Such field of view constraints may be modeled based on ray tracing performed within a model of the physical environment.

One or more kinematic constraints of the robot are identified at 610. In some embodiments, a robot may have a maximum or minimum height, orientation range, or other such physical limitations associated with the positions or orientations in which a UV end effector may be located or through which the UV end effector may be moved. Such kinematic constraints may be identified at least in part based on configuration parameters associated with the robot. Alternatively, or additionally, kinematic constraints may be dynamically determined. For instance, the robot may determine that its range of motion in a particular area is limited by the presence of a human, animal, or static object that blocks its effective motion range.

One or more safety constraints are identified at 612. According to various embodiments, a safety constraint may be, for instance, a maximum level of UV exposure associated with a human, an animal, a plant, or an inanimate object within an environment. However, some types of safety constraints may relate to the mobility of the robot itself. For instance, one safety constraint may preclude the robot from traveling too near the top of a stairway or the edge of a precipice. Another type of safety constraint may preclude the robot from traveling or positioning its appendages too near a dangerous area such as a roadway. Yet another type of safety constraint may cause the robot to exercise caution when moving into an area that the robot cannot observe from its current vantage point.

A desired level of ultraviolet light exposure is identified at 614. According to various embodiments, the desired level of ultraviolet light exposure may be determined based at least in part on the type and/or level of cleaning being performed. For example, for fast and light cleaning between frequent touches, a lower level of exposure may be set, whereas for full disinfection a higher level of exposure may be used. As another example, higher levels of exposure may be employed for some pathogens than for other pathogens. As yet another example, higher levels of exposure may be employed in particular environments such as surgical theatres in hospitals. As still another example, lower levels may be employed in areas where humans are believed to be present.

In particular embodiments, one or more constraints or objectives not shown in FIG. 6 may be identified. For instance, one or more constraints related to the time or distance involved in executing a cleaning trajectory may be employed.

One or more uncertainty values are identified at 616. According to various embodiments, uncertainty values may be determined in any of a variety of ways. For example, an uncertainty value may be determined based on measurement error associated with a sensor reading. As another example, an uncertainty value may be determined based on a degree of statistical uncertainty associated with a predetermined model value such as a field of view constraint associated with the UV end effector.

In some implementations, an uncertainty value may be set artificially high in order to optimize on a particular parameter. For instance, uncertainty values may be set artificially high for position values associated with a UV end effector in order to determine a trajectory for the UV end effector.

A relative importance of the identified constraints is determined at 618. According to various embodiments, some constraints may be entirely inflexible. Examples of such constraints may include, but are not limited to, the safety of nearby humans and the physical capabilities of the robot itself. Other types of constraints may be somewhat flexible. Examples of flexible constraints may include, but are not limited to, preferences such as shortest paths and distances to maintain from humans, minimum and maximum UV exposure values for inanimate objects, and time required to execute a trajectory.

A trajectory that balances the identified constraints according to their relative importance is determined at 620. According to various embodiments, the trajectory may be determined by applying an optimizer to the model, as discussed throughout the application, such as with respect to FIGS. 1 and 2.

Figure 7:
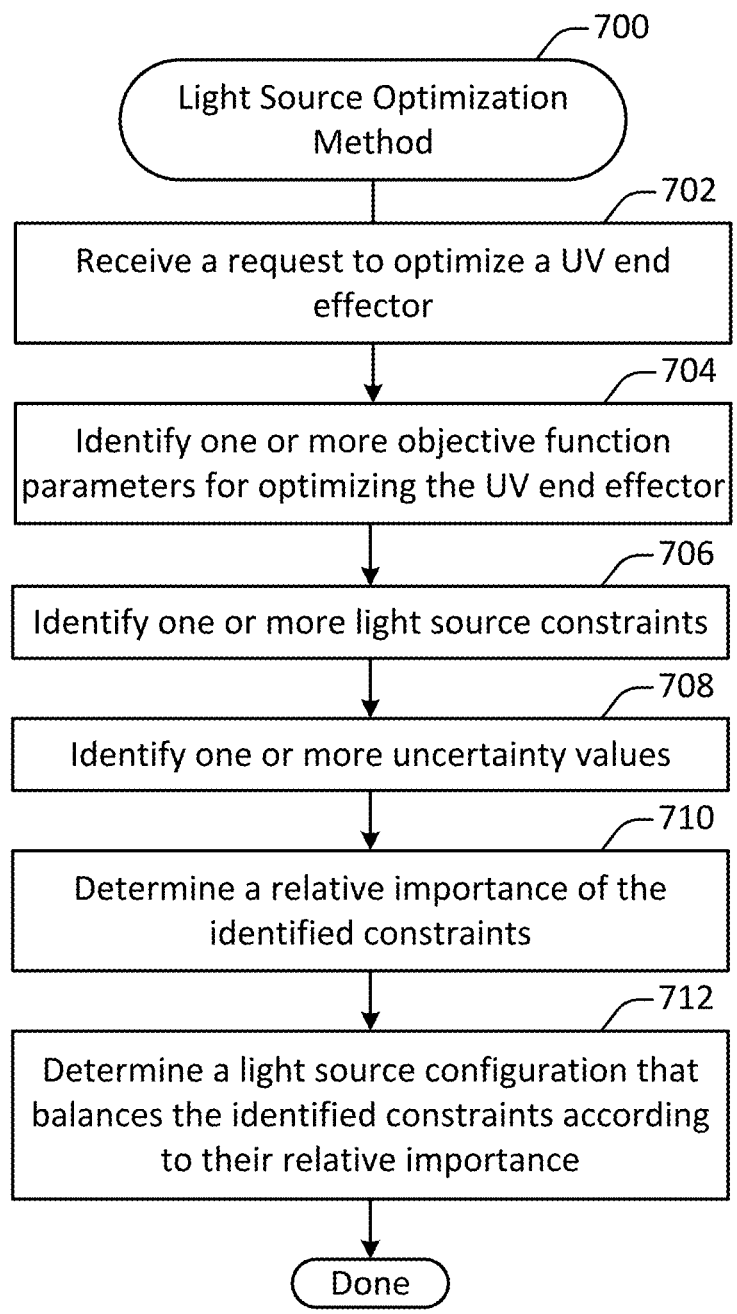
FIG. 7 illustrates a method for optimizing a light source, performed in accordance with one or more embodiments.

FIG. 7 illustrates a method 700 for optimizing a light source, performed in accordance with one or more embodiments. According to various embodiments, the method 700 may be performed in order to determine a configuration such as the number, position, orientation, and intensity of light sources on a UV end effector to achieve one or more objectives.

A request to optimize a UV end effector is received at 702. In some implementations, the method 700 may be performed as part of a development process, for instance to determine a static UV end effector configuration for a particular context. Alternatively, or additionally, the method 700 may be performed as part of the operation of a robot. For instance, a robot may be equipped with a reconfigurable UV end effector on which the position, number, orientation, and intensity of activated light sources may be dynamically reconfigured.

One or more objective function parameters for optimizing the UV end effector are identified at 704. According to various embodiments, the parameters may be specified as values in a model, as discussed for instance with respect to FIG. 2. Any of a variety of objective function parameters may be employed. For example, parameters may specify a desired level of UV exposure for a surface exposed to a UV end effector traveling along a particular trajectory at a particular speed. The method 700 may then be used to identify a configuration of light sources on the UV end effector to achieve the desired goal.

One or more light source constraints are identified at 706. According to various embodiments, light source constraints may include any suitable characteristics of the light sources that may be positioned on the UV end effector. For example, a light source may be equipped to handle a maximum or minimum power level. As another example, a light source may exhibit a particular intensity pattern, as discussed for instance with respect to the FIGS. 3-5. As yet another example, a light source may have a particular field of view limitation. As yet another example, a light source may have a particular range of possible locations and orientations on the UV end effector.

One or more uncertainty values are identified at 708. According to various embodiments, each uncertainty value may correspond with a different value within the model. As discussed herein, an uncertainty value may be specified in any of a variety ways, such as a standard deviation, a variance, or a statistical distribution.

A relative importance of the identified constraints is determined at 710. In some implementations, the relative importance may indicate a degree to which a particular constraint is flexible. For instance, a trajectory along which the UV end effector is intended to follow may be somewhat flexible, while a physical limitation of a light source may be inflexible.

In some implementations, one or more of the values discussed with respect to the operations 704-710 may be provided by an end user. Alternatively, one or more values may be determined by the robot itself, for instance by sensing a physical environment in which the robot is located.

A light source configuration is determined at 712 that balances the identified constraints according to their relative importance. In some implementations, the light source configuration may specify a location, orientation, number, intensity, or any other configurable characteristic of a light source located on a UV end effector. As discussed herein, for instance with respect to FIG. 2, the light source configuration may be determined by applying an optimizer to a model that includes the values identified at the operations 704-710.

Figure 8A:
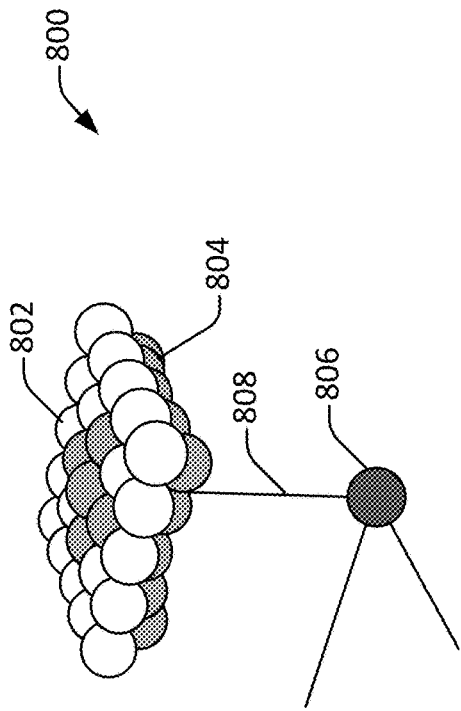
FIG. 8A and FIG. 8B illustrate diagrams of a simulated environment, generated in accordance with one or more embodiments.
Figure 8B:
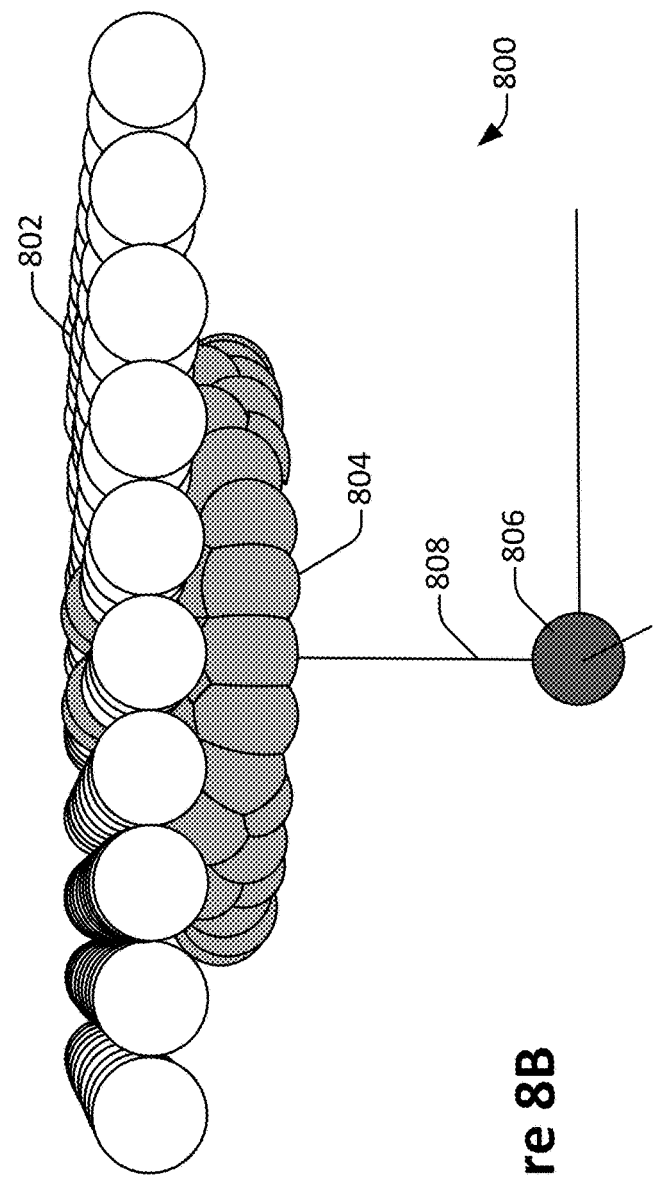

FIG. 8A and FIG. 8B illustrate diagrams of a simulated environment 800, generated in accordance with one or more embodiments. In the simulated environment 800, the blue sphere 806 represents a UV light source that may be used in conjunction with a UV end effector. The lines green line 808 represents a directional vector indicating a direction in which the light source 806 is pointed. The white spheres such as the sphere 802 represent the initial positions of points in a model that are configured to receive a designated amount of simulated ultraviolet irradiance within a designated period of time. The initial position values may be associated with high noise values. The orange spheres such as the sphere 804 represent updated positions for the points that are determined by solving the model to reduce the high noise values associated with the initial positions.

Figure 9A:
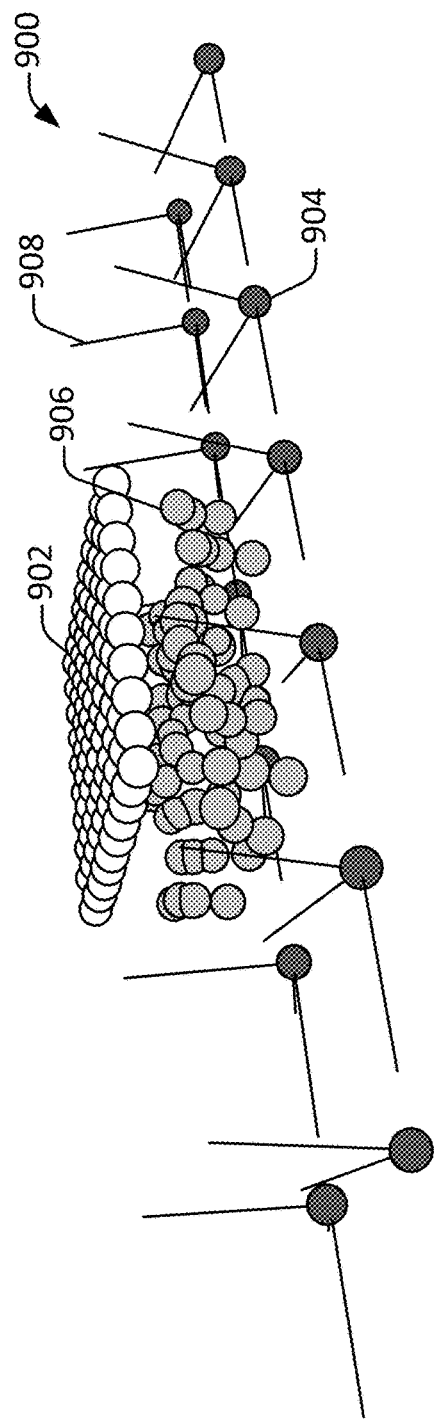
FIG. 9A and FIG. 9B illustrate diagrams of a simulated environment, generated in accordance with one or more embodiments.
Figure 9B:
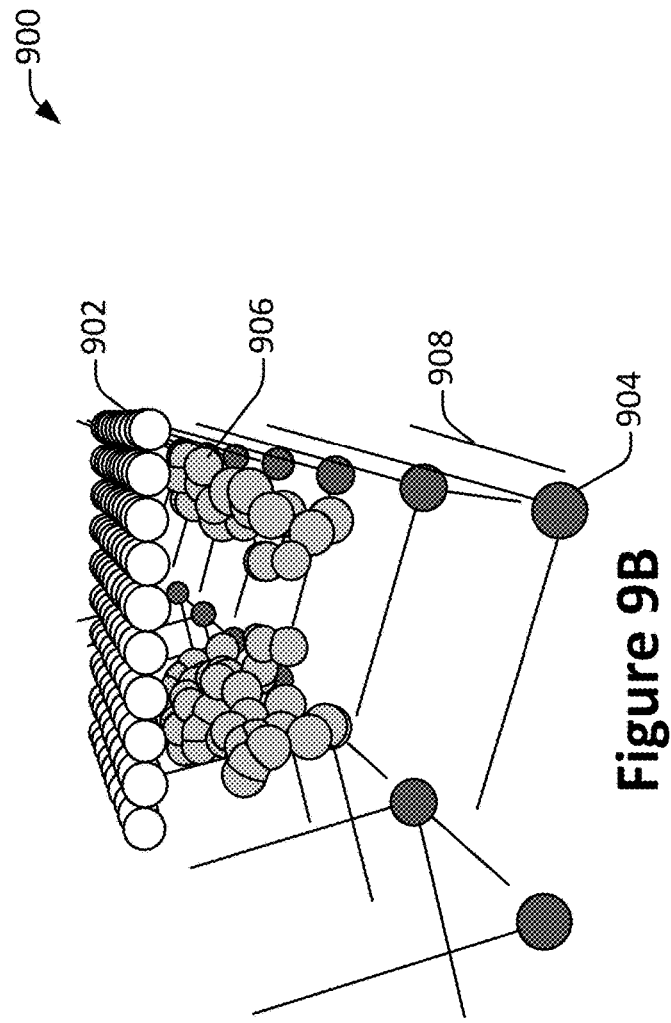

FIG. 9A and FIG. 9B illustrate diagrams of a simulated environment 900, generated in accordance with one or more embodiments. In the simulated environment 900, the blue spheres such as the sphere 904 represent UV light sources arranged on a paddle that may be used in conjunction with a UV end effector. The lines green lines such as the line 908 represent directional vectors indicating a direction in which each light source is pointed. The white spheres such as the sphere 902 represent the initial positions of points in a model that are configured to receive a designated amount of simulated ultraviolet irradiance within a designated period of time. The initial position values may be associated with high noise values. The green spheres at 906 represent updated positions for the points that are determined by solving the model to reduce the high noise values associated with the initial positions.

Figure 10:
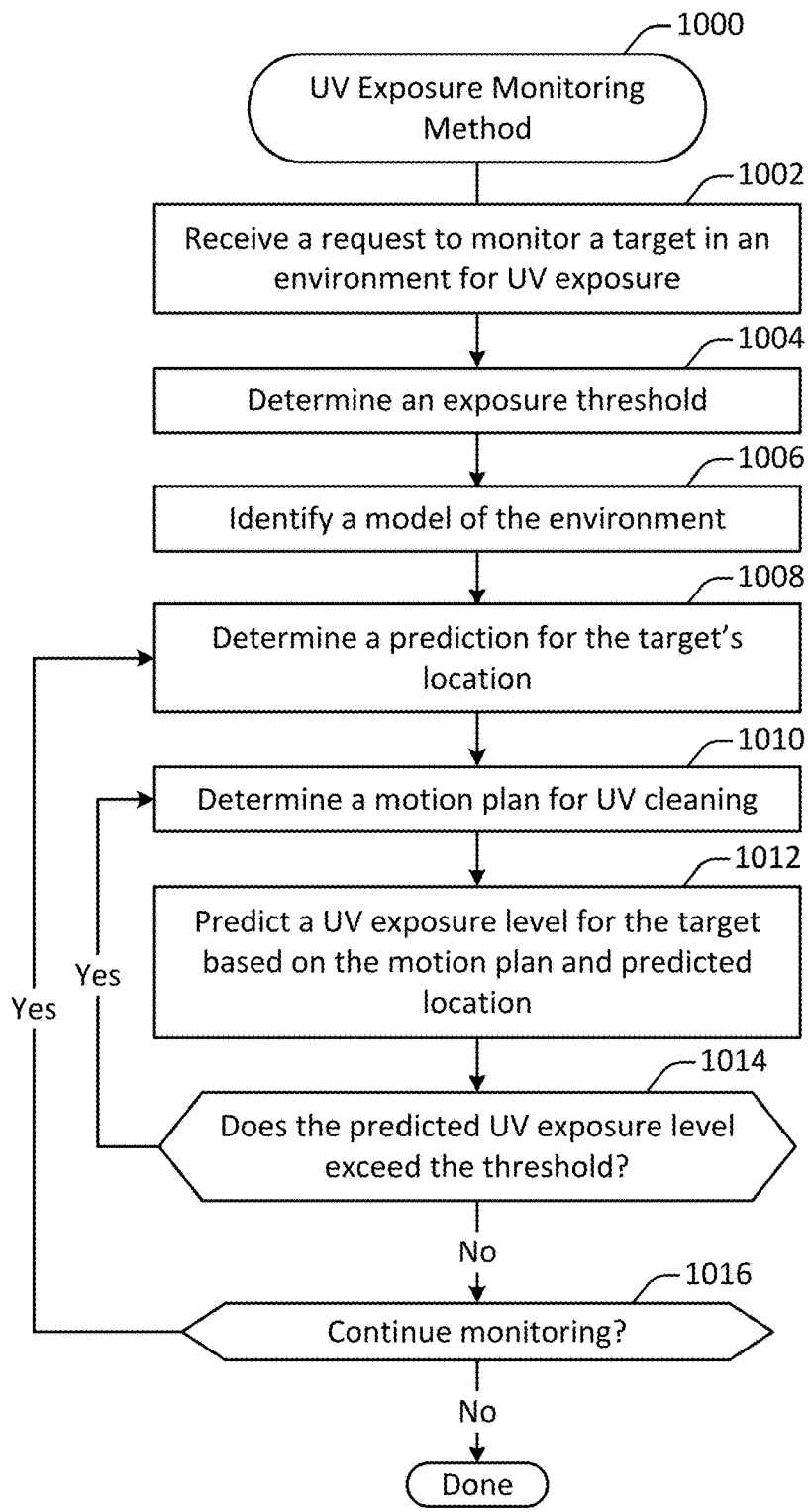
FIG. 10 illustrates a method for monitoring exposure to ultraviolet light, performed in accordance with one or more embodiments.

FIG. 10 illustrates a method 1000 for monitoring exposure to ultraviolet light, performed in accordance with one or more embodiments. According to various embodiments, the method 1000 may be used to monitor the exposure of a any suitable object or surface. Such objects or surfaces may include, but are not limited to: humans, animals, plants, and inanimate objects.

A request to monitor a target in an environment for UV exposure is received at 1002. In some implementations, the request may be generated based on user input. Alternatively, or additionally, a robot may autonomously initiate UV exposure monitoring when one or more conditions are met. For instance, the robot may autonomously initiate UV exposure monitoring when the robot is tasked with cleaning an area in or near which a human is present.

An exposure threshold is determined at 1004. According to various embodiments, the exposure threshold may be determined based on the type of target, the type of operation being performed, and other such considerations. For example, a human may be monitored for excessive exposure to ultraviolet light. In such a situation, the exposure of any point on the human's body to ultraviolet light that exceeds a designated threshold may be sufficient to avoid or terminate a cleaning plan. As another example, a surface to be cleaned may be monitored for adequate exposure to ultraviolet light. In such a situation, each monitored point on the surface may need to be exposed to ultraviolet light that exceeds a designated threshold.

In some implementations, different surfaces may have different thresholds. For example, a child may have a lower ultraviolet light exposure threshold than an adult. As another example, an animal may have a higher ultraviolet light exposure threshold than a human. As another example, different pathogens may have different levels of ultraviolet light exposure for disinfection.

A model of the environment is identified at 1006. According to various embodiments, the identification of a model at 1006 is substantially similar to corresponding operations discussed with respect throughout the application, such as with respect to FIGS. 1, 2, 6, and 7.

A prediction for the target's location is determined at 1008. According to various embodiments, the predicted location may be specified as a continues path through space over time. Alternatively, the predicted location may be specified as point locations at particular times.

In some implementations, the prediction may be associated with a noise value, which may increase the further in time the target's location is predicted. The prediction time may depend on considerations such as the length of time involved in the cleaning process, the magnitude of the noise value over time, or other such parameters.

In some implementations, the determination may be made based on factors such as the target's current location, past locations, velocity, acceleration, and other such characteristics. In particular embodiments, semantic information may be incorporated as well. For instance, in a hospital setting, a determination that a person is a doctor or a patient may lead to different predictions regarding the person's likely future location.

A motion plan for UV cleaning is determined at 1010. According to various embodiments, the motion plan may be determined for UV cleaning. In some implementations, the motion plan may be determined by applying an optimizer to the model, as discussed with respect to the method 700 shown in FIG. 7.

A UV exposure level for the target is predicted at 1012 based on the motion plan and the predicted location. In some implementations, the UV exposure level may be predicted by applying an optimizer to the model, as discussed with respect to FIG. 2.

Although in FIG. 7 operation 1008 is shown as preceding operation 1010, in various configurations the operations shown in FIG. 7 may be performed in a different order. For example, a motion plan for UV cleaning may be determined first. As another example, the motion plan for UV cleaning at 1010 may be determined contemporaneously with the predicted UV exposure level at 1012.

A determination is made at 1014 as to whether the predicted UV exposure level exceeds a designated threshold. If the designated threshold for UV exposure is predicted to exceed the threshold, then an updated motion plan is determined at 1010. The updated motion plan may include one or more of an altered trajectory, an altered intensity level or a cessation of cleaning. For instance, the robot may stop cleaning and wait until the human has left the area.

A determination is made at 1016 as to whether to continue monitoring. According to various embodiments, monitoring may continue until one or more conditions are met. For example, monitoring may continue until the target has moved out of an area, until cleaning has finished, or until a determination is made that the target is estimated to receive a level of UV exposure that exceeds a designated threshold.

Figure 14:
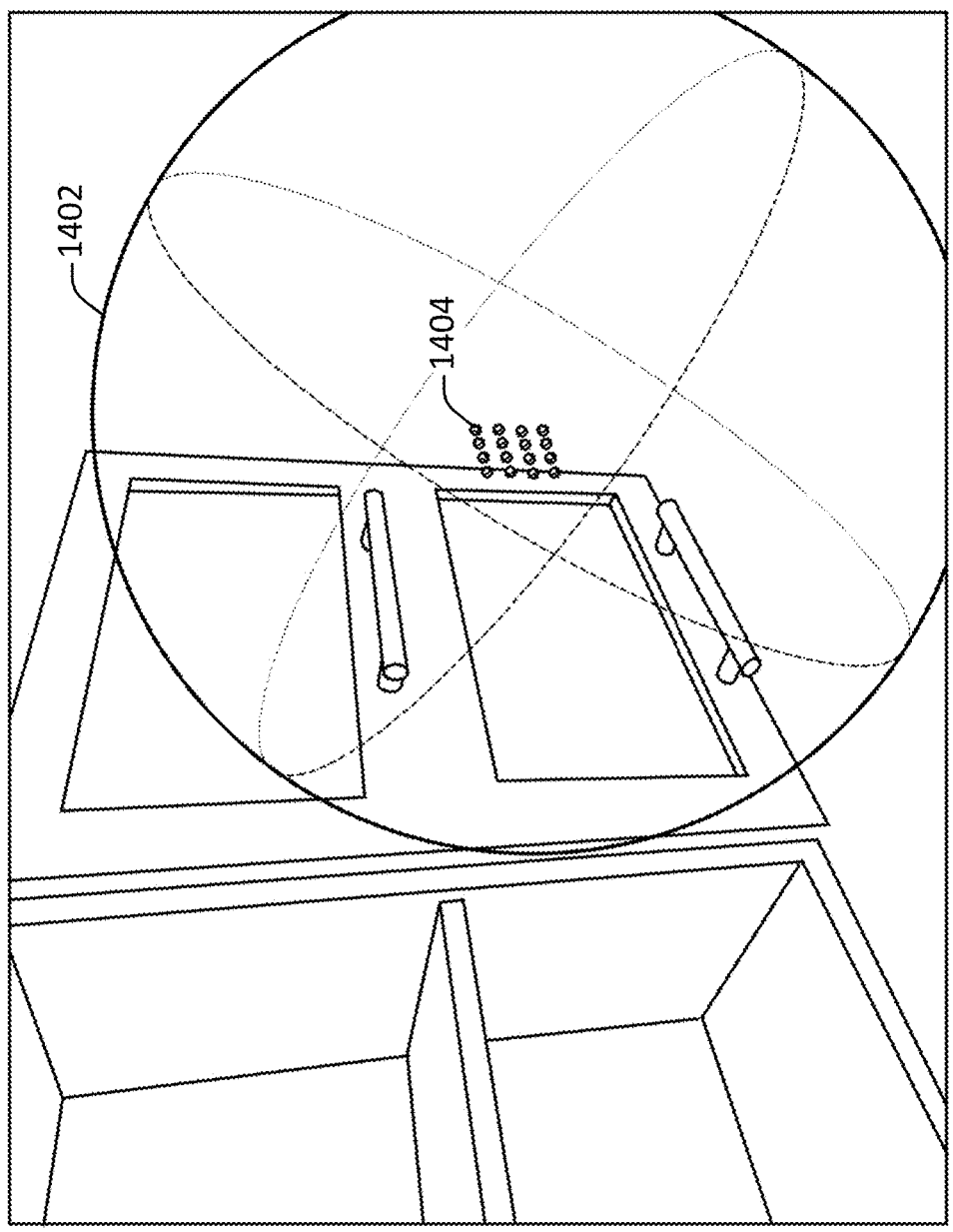
FIGS. 14, 15, and 16 illustrate models of exposure generated in accordance with one or more embodiments.

In particular embodiments UV exposure for may be estimated based on a three-dimensional model of a space. An example of such a model is shown in FIG. 14, where a sphere of exposure 1402 is estimated around an array of UV light sources 1404. The sphere expands over time as the UV light sources continue to operate in accordance with an exposure model. A similar approach may be used to estimate the dose received by a surface. In this way, the robot can ensure that a surface is cleaned by ensuring that the surface receives a dosage exceeding a first threshold while at the same time ensuring that humans are not exposed to UV radiation exceeding a second threshold.

In particular embodiments, a surface or object may be modeled as a mesh of vertices. The dose for a surface or object may then be estimated for each vertex of the surface or object. The surface or object is then determined to have received a sufficiently high dose when all vertices have received a dose exceeding a designated threshold.

Figure 15:
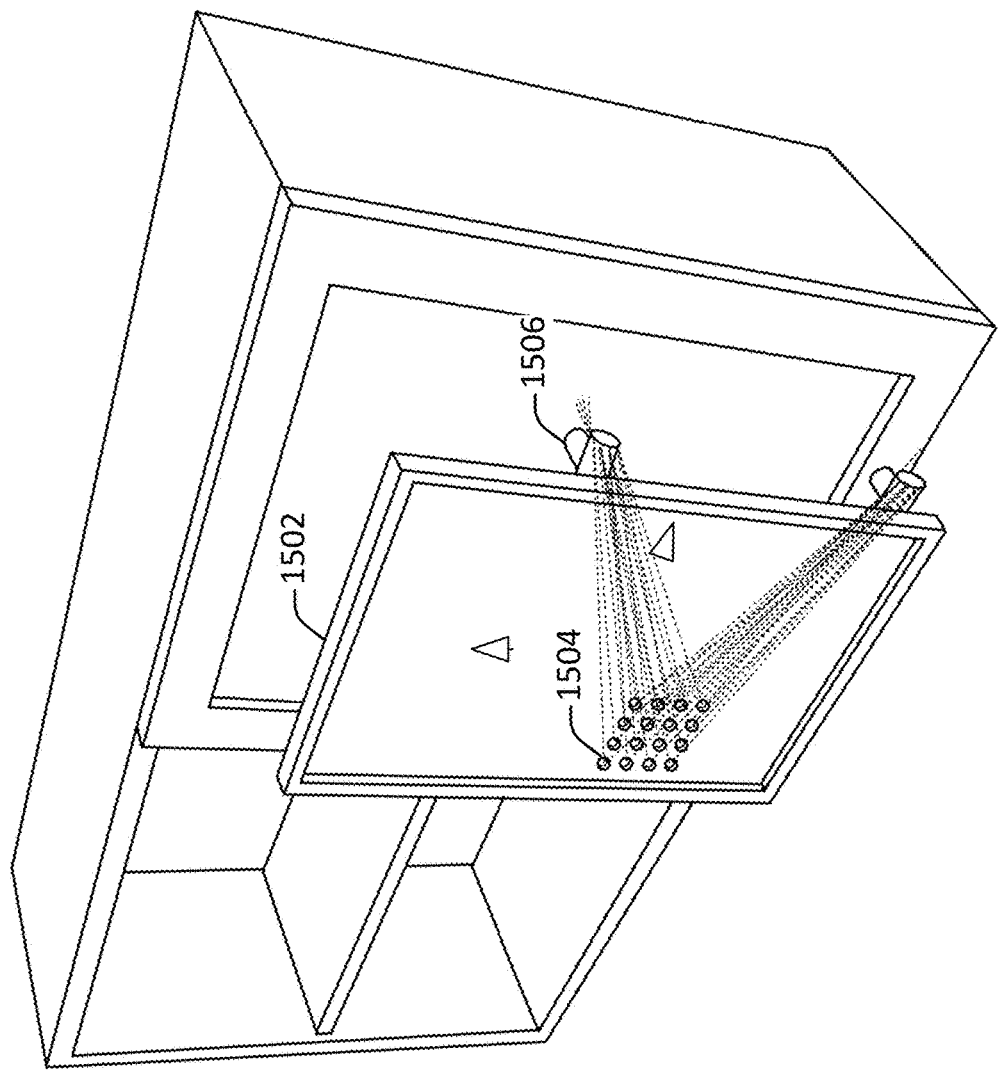
Figure 16:
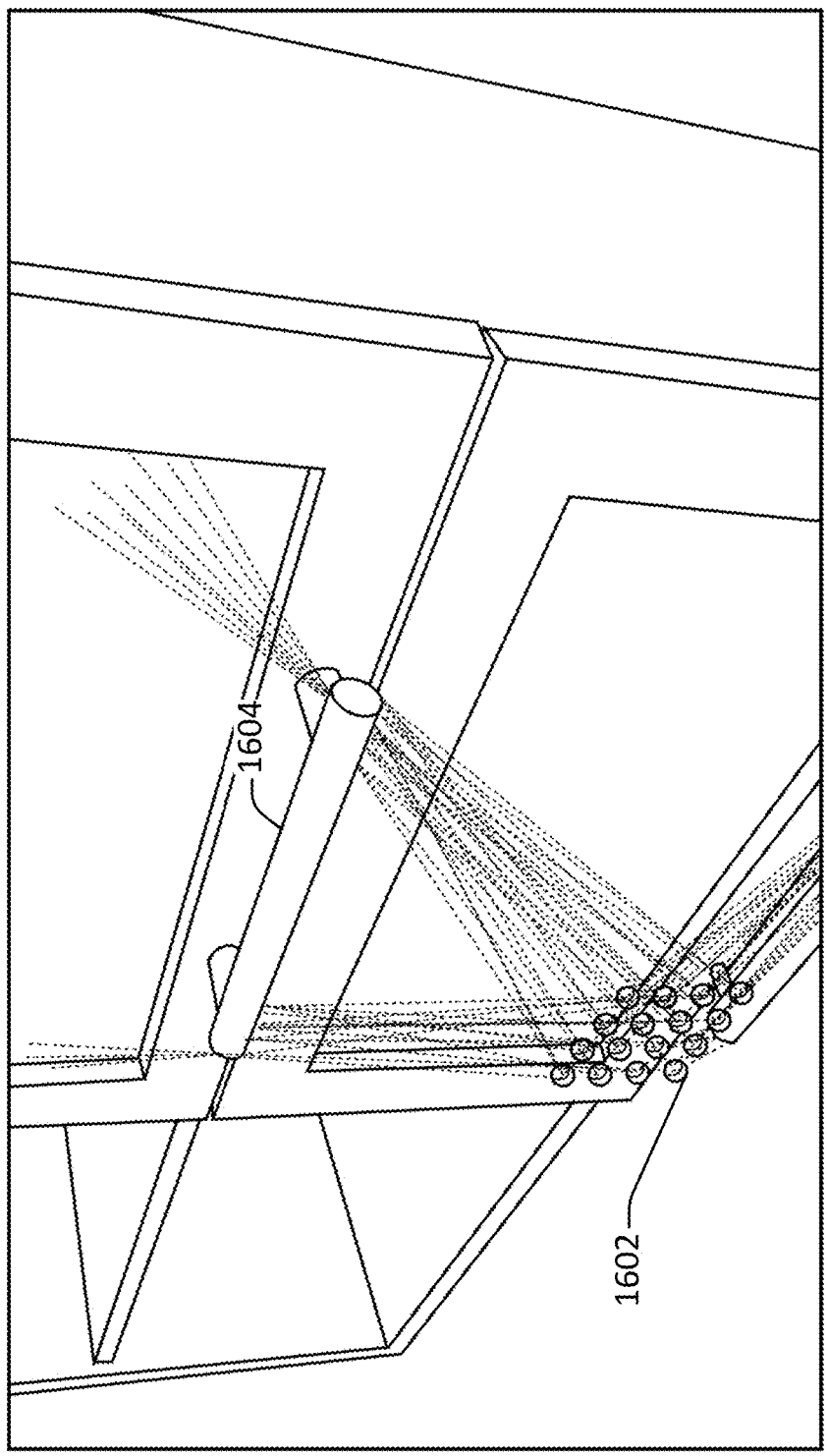

In particular embodiments, occlusions may be modeled with ray tracing as the light source, the object being cleaned, and/or one or more objects within the environment move. In this way, the dose received by an object or surface and/or the exposure received by a human may be more accurately modeled. An example of such an approach is shown in FIG. 15, where the plane 1502 represents a surface that has moved between the UV light array 1504 and the handle of the cabinet 1506. In particular embodiments, ray tracing may also be used to model the field of view of the light source. For example, in FIG. 15, ray tracing has been used to estimate UV exposure at different parts of the cabinet handle 1506. Another example of such an approach with a light source having a 130-degree field of view is shown in FIG. 16, in which the UV array 1602 is projecting light onto the front and bottom of the handle 164.

In particular embodiments, the exposure for the human and/or the dosage for the surface or object may be periodically transmitted to a remote location such as a database system via wireless communication. The cleaning robot may also receive data on exposure from the remote location. In this way, an accurate exposure level for a human may be estimated even when a human is near more than one cleaning robot during a period of time.

Figure 11:
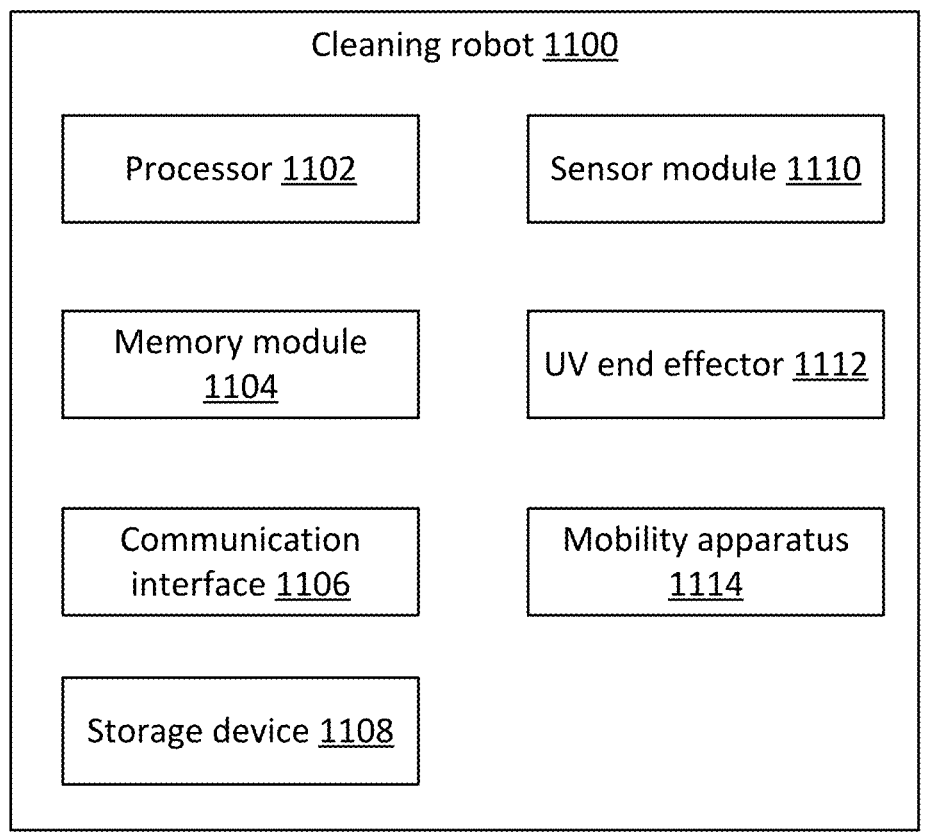
FIG. 11 illustrates a method for cleaning an area, performed in accordance with one or more embodiments.

FIG. 11 illustrates an architecture diagram for a cleaning robot 1100, configured in accordance with one or more embodiments. According to various embodiments, the cleaning robot 1100 may be configured in a variety of form factors so long as it includes the ability to relocate and clean a surface. The cleaning robot 1100 includes a processor 1102, a memory module 1104, a communication interface 1106, a storage device 1108, a sensor module 1110, a UV end effector 1112, and a mobility apparatus 1114.

According to various embodiments, the cleaning robot 1100 may include one or more processors 1102 configured to perform operations described herein. The memory module 1104 may include one or more transitory memory elements, such as random access memory (RAM) modules. The storage device 1108 may be configured to store information such as computer programming language instructions and/or configuration data.

In some implementations, the cleaning robot 1100 may include one or more communication interfaces 1106 configured to perform wired and/or wireless communication. For example, the communication interface 1106 may include a WiFi communication module. As another example, the communication interface 1106 may include a wired port such as a universal serial bus (USB) port, which may be connected when the cleaning robot couples with a docking or charging port or device.

According to various embodiments, the sensor module 1110 may include one or more of various types of sensors. Such sensors may include, but are not limited to: visual light cameras, infrared cameras, microphones, Lidar devices, Radar devices, chemical detection devices, near field communication devices, and accelerometers.

In particular embodiments, the sensor module 1110 may communicate with one or more remote sensors. For example, an environment may be equipped with one or more of various types of sensors, data from which may be relayed to cleaning robots within the vicinity.

According to various embodiments, the UV end effector 1112 may include one or more of a variety of suitable cleaning devices. Various types of UV light sources may be used. For example, a "point" LED may emit UV light, potentially with an angular range of emission. As another example, a cylindrical UV light may emit UV radiation in a relatively constant pattern along the axis of the cylinder and may potentially cover an angular range. Such sources may be combined in a fixed or variable pattern, for instance to provide a more powerful light source and/or to shape the UV emission pattern.

In particular embodiments, shielding may help to stop UV light from emitting in certain directions. Alternatively, or additionally, one or more reflectors or lenses may be used to help guide or focus UV light toward a target.

According to various embodiments, a cleaning device may be attached to the cleaning robot 1100 in any of various ways. For example, the cleaning device may be attached in a fixed orientation relative to a robot drive mechanism. As another example, the cleaning device may be attached to the cleaning robot via a robotic arm having any of a variety of possible geometries.

In particular embodiments, a UV light may be fixed in a downward pointing on a robotic arm having three degrees of freedom of spatial mobility, allowing the arm to be positioned at different points of space along three axes. In such a configuration, the cleaning device could be positioned to clean a table top by positioning the UV light at a designated distance from the table top through a combination of movement of the robotic arm and the robot itself. The cleaning device could be positioned in a fixed location over the table top, or could clean the table top from different locations. For example, larger table tops may require cleaning from more locations.

In particular embodiments, a UV light may be configured with four, five, six, or more degrees of freedom. For example, a robotic arm may have three degrees of freedom. Then, a UV light positioned on the arm may itself be configured for movement in three dimensions. In this case, the movement of the robotic arm and the UV light may be combined to trace a potentially complex trajectory through space in order to irradiate a target from multiple directions. For instance, a cleaning device may be configured with 5 degrees of freedom in order to irradiate a spherical door handle from the left, from the right, from above, and from below without requiring the robot itself to move.

According to various embodiments, the mobility apparatus may include one or more of any suitable mobility devices. Such devices may include, but are not limited to, one or more motorized wheels, balls, treads, or legs. In some configurations, the mobility apparatus may include one or more rotational and/or gyroscopic elements configured to aid in mobility and/or stability.

In particular embodiments, the cleaning robot 1100 may be configured to communicate directly or indirectly with other robots in order to accomplish its tasks. For example, robots may share information to build up an accurate model of an environment, identify the location and/or trajectory of humans, animals, or objects, perform social accommodation. As another example, robots may coordinate to execute a cleaning plan. For instance, one cleaning robot may be interrupted in a task due to social accommodation. The cleaning robot may then move on to another cleaning task, while a different cleaning robot may then later perform the interrupted cleaning task. As yet another example, robots may coordinate to perform a single task. For example, one or two robots may position themselves so as to provide social cues such as warning lights or sounds, while another robot engages in high-intensity UV cleaning in a designated area.

Figure 12:
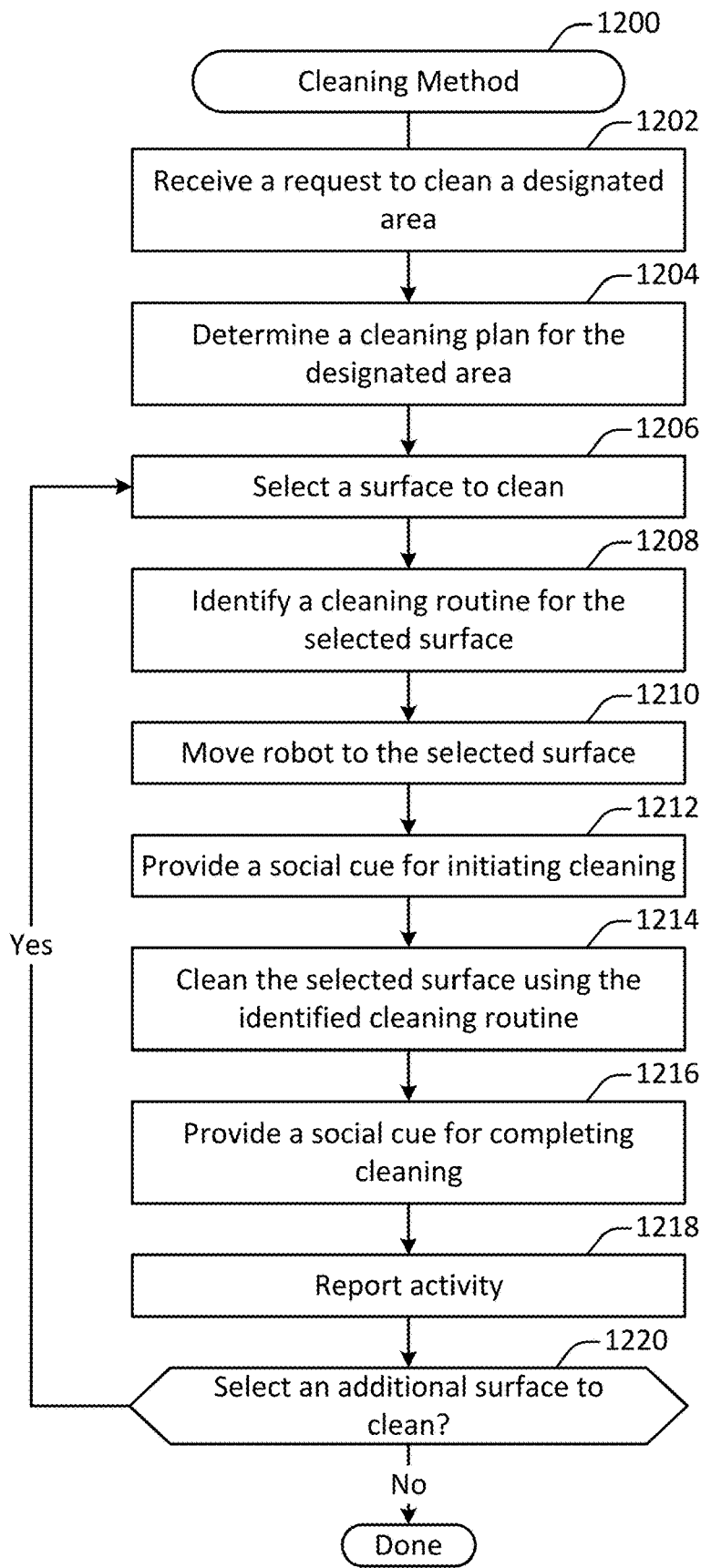
FIG. 12 illustrates a method for cleaning an area, performed in accordance with one or more embodiments.

FIG. 12 illustrates a method 1200 for cleaning an area, performed in accordance with one or more embodiments. The method 1200 may be performed by a cleaning robot such as the robot 100 shown in FIG. 1. The method 1200 may be performed as an example of a task as discussed with respect to the operations 202 and 204 shown in FIG. 2.

A request to clean a designated area is received at 1202. According to various embodiments, instructions for where and when to clean can be received from any of multiple sources. For example, a robot may receive instructions from a remote location such as a command center or cleaning service executed on a computing device. As another example, people in an environment may interact with a robot and ask it to perform a cleaning task once or on a regular basis.

According to various embodiments, instructions for where and when to clean can be general or specific. For example, an instruction may specify a particular location and a time at which to clean it. As another example, an instruction may specify a timing constraint associated with a location, such as cleaning every office door handle in a hallway twice per day. In this case, the robot may develop its own plan and then perform its own execution monitoring.

In some implementations, instructions for where and when to clean can be determined automatically. For example, the cleaning robot may monitor humans as part of its cleaning activity. As part of this monitoring, the cleaning robot may annotate the areas, surfaces, and objects that humans touched, were near to, sneezed on, or otherwise interacted with. Those areas may then be prioritized for cleaning. Human activity may also be determined based on data received from external sensors. For example, a room's motion sensor may indicate that no one has been there, so it may not need to be re-cleaned. As another example, a door sensor may identify a number of people who have visited a room such as a restroom, which may be targeted for recleaning after a threshold number of people have visited the room.

A cleaning plan for the designated area is determined at 1204. According to various embodiments, a cleaning plan for a designated area may include, for example, a list of surfaces and/or regions within an area to clean, as well as a path for navigating to each surface and/or region. The cleaning plan may be determined based on any of various considerations, such as the current and predicted location of people within the area, the time required to conduct the cleaning operations, and the distance traveled along the path. For instance, the robot may attempt to first minimize disruption to human activity and then minimize the cleaning time and distance traveled.

A surface to clean is selected at 1206. According to various embodiments, the cleaning robot may select a surface to clean based on the cleaning plan at 1204. For example, the cleaning robot may attempt to clean each doorknob in a hall or each table in a cafeteria in succession. However, the cleaning robot may adapt its plan in real time to accommodate changes to the environment, such as the actions of people. For example, the cleaning robot may skip a door that is open or a table that is occupied and return the door or table at a later point when it detects that the surface is not in use by humans.

A cleaning routine for the selected surface is identified at 1208. According to various embodiments, cleaning different types of objects and surfaces may involve different types of cleaning routines, which may change depending on the type of cleaning conducted. Accordingly, the specific pattern employed may depend on characteristics such as the strength of the UV light, characteristics of the environment, and the level of cleaning desired.

In some implementations, a small planar surface may be cleaned by holding a UV light fixture at a single point above it. A computation may be performed indicating the location of the point and how long the UV fixture needs to remain in place to meet the cleaning goal.

In some implementations, a large planar surface may be cleaned by moving a UV light fixture along a path in an X/Y plane parallel to the surface separated by a fixed distance Z. A computation may be performed to determine the distance Z, the path over the surface, and the speed at which the path is traversed to meet the cleaning goal.

In some implementations, a planar surface may be cleaned by moving a UV light fixture along a path in an X/Y plane parallel to the surface separated by a variable distance Z. For example, near the middle of the surface a higher intensity light may be applied at a larger distance Z, while near the edge of the surface a lower intensity light may be applied at a smaller distance Z to reduce spillover to areas behind the surface. A computation may be performed to determine the variable distance Z, the path over the surface, and the speed at which the path is traversed to meet the cleaning goal.

In some implementations, a surface such as one or more elevator call buttons, one or more internal elevator buttons, and/or small areas around buttons may be cleaned by emitting UV light on a line perpendicular to the plane of the button surface.

In some implementations, non-planar or elongated shape such as a faucet or handle may be cleaned via a vertical scan with a horizontal UV light emission coupled with an arc around the axis of the handle. The trajectory may change depending on the shape of the handle. For example, the robot may have a handle cleaning routine that it can adapt to a particular handle via rotation of a cleaning arm. As another example, spherical knobs may be cleaned via a rotational path around the knob.

According to various embodiments, the cleaning routine for the selected surface may be identified via one or more of a variety of techniques. In some implementations, cleaning routines for a fixed environment may be preprogrammed. For example, a robot may be manually configured to clean different surfaces or objects in an area in particular ways. As another example, a robot may be pre-configured to clean a standardized area such as a chain restaurant building, prefabricated housing area, hotel room, office hallway, retail location, or other such place.

In some implementations, different categories of objects and surfaces may each be associated with a specific cleaning routine. One or more of the cleaning routines may be parameterized. For instance, a procedure for cleaning a planar surface may be parameterized based on the size of the surface. Each object or surface may be pre-categorized by a human in advance. Alternately, or additionally, a trained neural network may be applied to categorize objects based on sensor data.

In some implementations, a cleaning robot may automatically determine a cleaning routine based on sensor data. For example, visual data and/or 12D scanning data may be used to estimate a three dimensional shape of the object or surface to be cleaned. A 12D planner may then be used to plan the trajectory and timing of the cleaning.

In some implementations, a cleaning robot may receive external information such as user input from a person, a two-dimensional or three-dimensional model or drawing of a region, surface, or object, a pre-trained neural network, or other such guidance.

According to various embodiments, a cleaning robot may use any technique in isolation to determine a cleaning plan. Alternately, or additionally, techniques may be used in combination. For example, a cleaning robot may be pre-configured to clean a variety of fixed environments. The cleaning robot may then be configured with specific cleaning routines for specific categories of objects. The cleaning robot may also be capable of automatically determining a cleaning routine based on sensor data, for instance when an object does not fall into an identified category. Finally, the cleaning robot may be configured to clean an object or surface based on user input, for instance when other approaches are insufficient for completing a cleaning task.

The cleaning robot is moved to the selected surface at 1210. In some implementations, moving the cleaning robot to the selected surface may involve engaging a mobility mechanism such as one or more wheels or treads. Additionally, the robot may need to navigate around obstacles such as people, animals, objects, or other robots. The robot may conduct that navigation in a socially accommodating manner. For example, the robot may move out of the way of humans, animals, or other robots, even though such accommodation requires moving along a longer path or waiting until a path is clear. As another example, the robot may predict the movement of humans, animals, or other robots in order to plan a path that avoids collisions.

A social cue for initiating cleaning is provided at 1212. According to various embodiments, any of a variety of social cues may be employed. Examples of such cues may include, but are not limited to: lights, sounds, vibration, and movement. For example, a robot may activate one or more lights and/or emit one or more sounds when cleaning is initiated. As another example, the robot may activate a spinning mechanical component to provide a visual indicator associated with cleaning.

In particular embodiments, a robot may emit a visual social cue indicating how long a task will take. For example, a robot may be equipped with a visible screen that is configured to display one or more countdown clocks. A countdown clock may indicate a time remaining for cleaning a specific surface or object. Alternately, or additionally, a countdown clock may indicate a time remaining for cleaning an entire area. As another example, a cleaning robot may be equipped with one or more colored lights to indicate the degree of completion of a task. For instance, presenting a visual cue may involve changing the color of an LED strip. The visual social cue may be perceivable from a distance so that a human can decide whether to interrupt the robot.

In some embodiments, presenting a visual cue may involve emitting audio. For example, one or more sound effects may be emitted when people transition across virtual boundaries. As another example, audio communication may be emitted in the form of music. As yet another example, audio communication may be emitted in the form of spoken natural language, for instance via text to speech or voice recording. Natural language communication may be presented on a display screen, or through speech, or a combination thereof. As still another example, the cleaning robot may emit a tune or whistle to indicate its progression in a cleaning cycle. As still another example, the cleaning robot may be configured to emit a verbal countdown or other natural language descriptions of progress along a task. For instance, the cleaning robot may state a task and verbally identify the initiation and/or completion of a task.

In some embodiments, presenting a visual cue may involve an information screen configured to display information such as text or icons. For instance, a caution icon may be displayed.

In some embodiments, presenting a visual cue may involve a projector to display information similarly to screen displays. Alternatively, or additionally, a projector may present a visual cue through illumination based on color and/or brightness similarly to LED strips. A projector may be used to show a graphic and/or text on the ground, for instance to indicate a safe boundary for humans to stay away, or onto a surface being disinfected, for instance to display AR information.

In some embodiments, a display screen on the robot may display an emotionally expressive face that is used for indicating system states. For example, when people are detected, the robot may present a happy face. As another example, when people are engaged in interaction for communicating with the robot, the robot may present a face that reflects the situation or statement (e.g., happy, apologetic, or thankful). As yet another example, when the robot predicts that people may soon be in an unsafe location, the robot may display a face indicating shock or panic.

In some embodiments, presenting a visual cue may involve motion. For example, the robot may use its arm for communicative gestures such as pointing to objects or surfaces for confirmation or socially communicating with people, for instance by waving. As another example, the robot may have the ability to move a "head" area (e.g., with 1-3 degrees of freedom) on which a display screen is mounted to control head gaze for communicating with people and directing sensors. Head gaze direction may be used to communicate task state (e.g., navigational goals, object/surface targets for disinfection) or interaction state (e.g., people being interacted with). Neck motions may also be used as communicative gestures, such as shaking the head no. As yet another example, the robot may use a mobile base trajectory for communication, for instance by driving to encircle a region to refer to it for task confirmation. As still another example, any of the robot's movable components may be used for emphasis within a communicative message, for instance for beat gestures.

The selected surface is cleaned using the identified cleaning routine at 1214. In some implementations, cleaning the selected surface may involve operations such as adjusting the position of the cleaning robot, adjusting the position of one or more cleaning devices, and/or adjusting one or more settings associated with a cleaning device such as the intensity of UV light emitted. For instance, a UV light may be activated and strengthened or weakened in intensity as it is moved through space in an arc around a circular object or in a plan over a flat object.

A social cue for completing cleaning is provided at 1216. In some implementations, the social cue for completing cleaning may simply involve no longer emitting the social cue for initiating cleaning provided at 1212. Alternately, or additionally, a different social cue may be emitted to demonstrate that cleaning has stopped. For instance, a robot may emit a green light when not cleaning and a red light while cleaning.

In particular embodiments, a cleaning robot may strategically determine a social cue based on factors such as environmental characteristics. For example, the cleaning robot may emit a brighter light or louder sound in a brighter or louder environment with more people, while emitting a dimmer light or quieter sound in a darker or quieter environment.

Activity is reported at 1218. According to various embodiments, the activity may be reported via the communication interface 106 shown in FIG. 1. The cleaning robot may report on any or all activity. For example, the cleaning robot may report on cleaning activity such as where it cleaned, when it cleaned, and/or one or more parameters of the cleaning process. As another example, the cleaning robot may report on social accommodation actions such as when, where, why, and how it took action to accommodate activity by humans, animals, or other robots. As yet another example, the cleaning robot may report on characteristics of the environment observed via its sensors, such as the presence or absence of trash, graffiti, or damage. As still another example, the cleaning robot may report on successes, failures, and/or reasons for failure while executing its cleaning plan.

In some implementations, activity may be reported in real time. For example, a robot may communicate with a remote database via WiFi. Alternatively, or additionally, activity may be reported via bulk communication. For example, a robot may transmit a comprehensive log of activity, for instance via a wired connection, when the robot returns to a charging or docking station.

A determination is made at 1220 as to whether to select an additional surface to clean. In some implementations, the determination may be made at least in part on whether the cleaning robot has cleaned each surface according to the cleaning plan determined at 102. For instance, the cleaning robot may revisit a surface that it was initially unable to clean due to accommodating people within the environment.

In particular embodiments, one or more of the operations shown in FIG. 12 may be omitted. For example, the cleaning robot may not provide a social cue in some configurations, such as in settings where limited light and sound disruption is desired.

Figure 13:
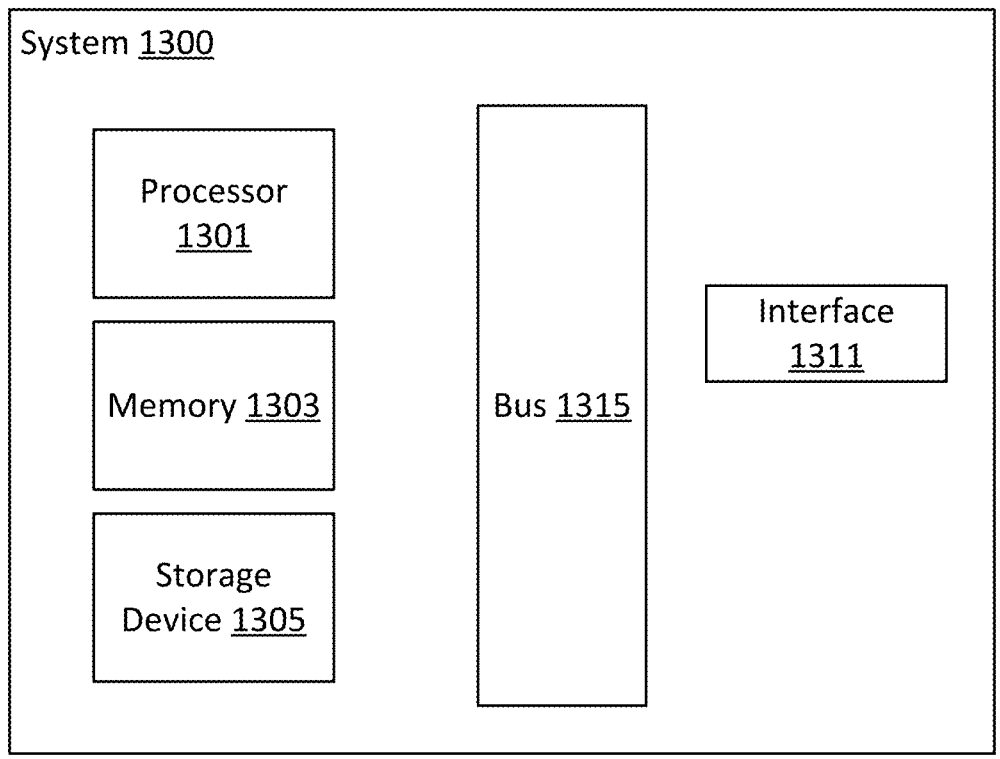
FIG. 13 illustrates one example of a computing device.

FIG. 13 illustrates one example of a computing device. According to various embodiments, a system 1300 suitable for implementing embodiments described herein includes a processor 1301, a memory module 1303, a storage device 1305, an interface 1311, and a bus 1315 (e.g., a PCI bus or other interconnection fabric.) System 1300 may operate as variety of devices such as cleaning robot, remote server, or any other device or service described herein. Although a particular configuration is described, a variety of alternative configurations are possible. The processor 1301 may perform operations such as those described herein. Instructions for performing such operations may be embodied in the memory 1303, on one or more non-transitory computer readable media, or on some other storage device. Various specially configured devices can also be used in place of or in addition to the processor 1301. The interface 1311 may be configured to send and receive data packets over a network. Examples of supported interfaces include, but are not limited to: Ethernet, fast Ethernet, Gigabit Ethernet, frame relay, cable, digital subscriber line (DSL), token ring, Asynchronous Transfer Mode (ATM), High-Speed Serial Interface (HSSI), and Fiber Distributed Data Interface (FDDI). These interfaces may include ports appropriate for communication with the appropriate media. They may also include an independent processor and/or volatile RAM. A computer system or computing device may include or communicate with a monitor, printer, or other suitable display for providing any of the results mentioned herein to a user.

In the foregoing specification, various techniques and mechanisms may have been described in singular form for clarity. However, it should be noted that some embodiments include multiple iterations of a technique or multiple instantiations of a mechanism unless otherwise noted. For example, a system uses a processor in a variety of contexts but can use multiple processors while remaining within the scope of the present disclosure unless otherwise noted. Similarly, various techniques and mechanisms may have been described as including a connection between two entities. However, a connection does not necessarily mean a direct, unimpeded connection, as a variety of other entities (e.g., bridges, controllers, gateways, etc.) may reside between the two entities.

In the foregoing specification, reference was made in detail to specific embodiments including one or more of the best modes contemplated by the inventors. While various implementations have been described herein, it should be understood that they have been presented by way of example only, and not limitation. For example, some techniques and mechanisms are described herein in the context of cleaning via UV light. However, the techniques of the present invention apply to a wide variety of cleaning techniques. Particular embodiments may be implemented without some or all of the specific details described herein. In other instances, well known process operations have not been described in detail in order not to unnecessarily obscure the present invention. Accordingly, the breadth and scope of the present application should not be limited by any of the implementations described herein, but should be defined only in accordance with the claims and their equivalents.

The invention claimed is:

1. A method comprising:
   determining via a processor a model of a physical environment based at least in part on sensor data collected by one or more sensors at a robot, the model including a plurality of constraints including a field of view constraint indicating a field of view associated with an ultraviolet end effector coupled with the robot and including one or more ultraviolet light sources, the model further including a plurality of data values including a location of a human within the physical environment, the model further including a plurality of original uncertainty values expressing a statistical dispersion around a respective one of a subset of the data values including the location of the human;

determining, via the processor and based on the model, a trajectory through the physical environment for the ultraviolet end effector to clean one or more surfaces in the physical environment such that an estimated UV exposure level for the human is below a designated threshold, wherein determining the trajectory involves determining a plurality of updated data values corresponding with the subset of the data values and including a predicted location of the human, and wherein determining the trajectory involves determining the estimated UV exposure level for the human based on the predicted location, the uncertainty values, the field of view constraint, and the trajectory; and causing the ultraviolet end effector to move along the trajectory.

2. The method recited in claim 1, wherein the uncertainty values account for a location uncertainty regarding one or more initial location values associated with the ultraviolet end effector, and wherein determining the trajectory involves reducing the location uncertainty.

3. The method recited in claim 1, wherein the determined trajectory is consistent with the uncertainty values.

4. The method recited in claim 1, wherein the model is encoded as a factor graph.

5. The method recited in claim 1, wherein the plurality of constraints includes a visibility constraint associated with the physical environment, the visibility constraint indicating a physical occlusion within the physical environment.

6. The method recited in claim 1, wherein each of the constraints is associated with a respective relative importance value within the model, and wherein the trajectory is determined at least in part based on the relative importance values.

7. The method recited in claim 1, wherein the plurality of constraints includes a kinematic constraint indicating a physical limitation associated with the movement of the robot through the physical environment.

8. The method recited in claim 1, wherein the plurality of constraints includes a designated level of ultraviolet light to be received by the one or more surfaces.

9. The method recited in claim 8, wherein the designated level of ultraviolet light is determined based on an identity of one or more pathogens to be cleaned from the one or more surfaces.

10. The method recited in claim 1, wherein the plurality of constraints includes an energy constraint indicating a level of energy capable of being expended by the robot.

11. The method recited in claim 1, wherein the model includes a cost function identifying a virtual cost associated with a time associated with the determined trajectory, and wherein determining the trajectory involves reducing the time based on the cost function.

12. The method recited in claim 1, wherein the model includes a cost function identifying a virtual cost associated with one or more types of movement by the robot, and wherein determining the trajectory involves reducing movement based on the cost function.

13. A robot comprising:
an ultraviolet end effector including one or more ultraviolet light sources;
a sensor configured to collect sensor data from a physical environment;
a processor configured to:
determine a model of a physical environment based at least in part on the sensor data, the model including a plurality of constraints including a field of view constraint indicating a field of view associated with an ultraviolet end effector coupled with the robot and including one or more ultraviolet light sources, the model further including a plurality of data values including a location of a human within the physical environment, the model further including a plurality of original uncertainty values expressing a statistical dispersion around a respective one of a subset of the data values including the location of the human, and
determine based on the model a trajectory through the physical environment for the ultraviolet end effector to clean one or more surfaces in the physical environment such that an estimated UV exposure level for the human is below a designated threshold, wherein determining the trajectory involves determining a plurality of updated data values corresponding with the subset of the data values and including a predicted location of the human, and wherein determining the trajectory involves determining the estimated UV exposure level for the human based on the predicted location, the uncertainty values, the field of view constraint, and the trajectory; and
a mobility apparatus configured to move the ultraviolet end effector along the trajectory.

14. One or more non-transitory computer readable media having instructions stored thereon for performing a method, the method comprising:
determining via a processor a model of a physical environment based at least in part on sensor data collected by one or more sensors at a robot, the model including a plurality of constraints including a field of view constraint indicating a field of view associated with an ultraviolet end effector coupled with the robot and including one or more ultraviolet light sources, the model further including a plurality of data values including a location of a human within the physical environment, the model further including a plurality of original uncertainty values expressing a statistical dispersion around a respective one of a subset of the data values including the location of the human;
determining, via the processor and based on the model, a trajectory through the physical environment for the ultraviolet end effector to clean one or more surfaces in the physical environment such that an estimated UV exposure level for the human is below a designated threshold, wherein determining the trajectory involves determining a plurality of updated data values corresponding with the subset of the data values and including a predicted location of the human, and wherein determining the trajectory involves determining the estimated UV exposure level for the human based on the predicted location, the uncertainty values, the field of view constraint, and the trajectory; and
causing the ultraviolet end effector to move along the trajectory.

* * * * *